US012708525B2

(12) United States Patent
Arcos et al.

(10) Patent No.: US 12,708,525 B2
(45) Date of Patent: Aug. 18, 2026

(54) INTERVERTEBRAL DEVICES

(71) Applicant: AXIS SPINE TECHNOLOGIES LTD, Reading (GB)

(72) Inventors: Jonathan Arcos, Reading (GB); Christopher Reah, Reading (GB); Nicholas Sandham, Reading (GB); David Powell, Reading (GB); John Sutcliffe, Reading (GB); Patrick Mckenna, Reading (GB)

(73) Assignee: AIS SPINE TECHNOLOGIES LTD, Reading (GB)

( * ) Notice: Subject to any disclaimer, the term of this patent is extended or adjusted under 35 U.S.C. 154(b) by 0 days.

(21) Appl. No.: 18/974,389

(22) Filed: Dec. 9, 2024

(65) Prior Publication Data

US 2025/0312171 A1 Oct. 9, 2025

Related U.S. Application Data

(63) Continuation-in-part of application No. 17/794,254, filed as application No. PCT/GB2021/050135 on Jan.

(Continued)

(30) Foreign Application Priority Data

Nov. 19, 2018 (GB) ...................................... 1818849
Jan. 21, 2020 (GB) ...................................... 2000890

(51) Int. Cl.
*A61F 2/44* (2006.01)
*A61F 2/46* (2006.01)

(Continued)

(52) U.S. Cl.
CPC ............ *A61F 2/447* (2013.01); *A61F 2/4611* (2013.01); *A61F 2002/2835* (2013.01); *A61F 2002/30476* (2013.01)

(58) Field of Classification Search
CPC ...... A61F 2/442; A61F 2/4425; A61F 2/4455; A61F 2002/443

(Continued)

(56) References Cited

U.S. PATENT DOCUMENTS

2007/0270968 A1* 11/2007 Baynham ................ A61F 2/447 623/17.11
2010/0280617 A1* 11/2010 Coppes ................ A61F 2/4425 623/17.16
2016/0151168 A1* 6/2016 Weiman .................... A61F 2/44 623/17.16

* cited by examiner

*Primary Examiner* — Eduardo C Robert
*Assistant Examiner* — Christina Negrellirodriguez
(74) *Attorney, Agent, or Firm* — LIU & LIU

(57) ABSTRACT

An intervertebral fusion device comprises an endplate, a core component and at least one ratchet. Each of the endplate and the core component has a leading end and a trailing end and is configured to be received in an intervertebral space defined between first and second vertebrae. The ratchet comprises a pawl and a linear rack defining plural recesses. The pawl is comprised in the core component or the endplate and the linear rack is comprised in the other of the core component and the endplate. The core component and the endplate are configured to engage with each other by disposing the leading end of the core component adjacent the trailing end of the endplate and then moving the core component relative to the endplate in a direction of insertion such that the leading end of the core component moves towards the leading end of the endplate and extent of overlap of the core component and the endplate increases. The plural recesses of the linear rack extend in the direction of insertion and from near or at one of the leading end and the trailing end of the other of the core component and the endplate towards the other of the leading end and the trailing end of the other of the core component and the endplate. The plural recesses extends by no more than 60% of a distance between (Continued)

the leading end and the trailing end. The ratchet is configured such that the pawl starts to inter-engage with the plural recesses of the linear rack as the core component is moved further relative to the endplate in the direction of insertion and such that the pawl progresses along the plural recesses with further movement of the core component until the core component and the endplate have a desired extent of overlap.

24 Claims, 14 Drawing Sheets

Related U.S. Application Data

21, 2021, now Pat. No. 12,161,561, application No. 18/974,389, filed on Dec. 9, 2024 is a continuation-in-part of application No. 17/841,648, filed on Jun. 15, 2022, now abandoned, which is a continuation-in-part of application No. 17/294,683, filed as application No. PCT/GB2019/053275 on Nov. 19, 2019, now Pat. No. 12,090,062.

(51) Int. Cl.
*A61F 2/28* (2006.01)
*A61F 2/30* (2006.01)

(58) Field of Classification Search
USPC ........................................... 623/17.11–17.16
See application file for complete search history.

312
313
319
315
317
322
324
321
321
319
317
332

312
315
330
313
322
321
324
321
326
328

INTERVERTEBRAL DEVICES

This application is: (a) a continuation-in-part of U.S. patent application Ser. No. 17/794,254 filed on Jul. 20, 20221, issuing as U.S. Pat. No. 12,161,561 on Dec. 10, 2024, which is a 371 of International Application No. PCT/GB2021/050135 filed on Jan. 21, 2021, which claims priority of GB Patent Application No. 2000890.0 filed on Jan. 21, 2020; and (b) a continuation-in-part of U.S. patent application Ser. No. 17/841,648 filed on Jun. 15, 2022, which is a continuation-in-part of U.S. patent application Ser. No. 17/294,683 filed on May 17, 2021, issued as U.S. Pat. No. 12,090,062 on Sep. 17, 2024, which is a 371 of International Application No. PCT/GB2019/053275 filed on Nov. 19, 2019, which claims priority of GB Patent Application No. 1818849.0 filed on Nov. 19, 2018. These applications are fully incorporated by reference as if fully set forth herein.

FIELD OF THE INVENTION

The present invention relates to intervertebral devices and more specifically to intervertebral fusion devices.

BACKGROUND ART

Adjacent vertebrae in the spinal column are coupled to each other by a number of ligaments and the intervertebral disc. These anatomic structures hold the adjacent vertebrae together while allowing motion. Among these structures, the intervertebral disc functions as a cushion between the vertebrae whilst allowing for relative movement of the vertebrae. Problems arise from one or more of a range of diseases and conditions. One such problem is spondylolisthesis, which is a slipping out of alignment of at least one vertebra and which occurs, in most cases, at the base of the spine. The misalignment is usually in the anterior-posterior direction. Spondylolisthesis is caused by degeneration of the discs or the supporting ligaments, a defect in or fracture of at least one of both wing-shaped parts of a vertebra, developmental problems or trauma to the pars.

A first known approach to addressing spondylolisthesis involves use of pedicle screws alone. This approach is normally used when the intervertebral disc has not been compromised to the extent that there is need to restore foraminal height. In this approach pedicle screws are placed above and below the affected part of the spine. The surgeon then manipulates the spine to address the spondylolisthesis. When the surgeon is satisfied with his or her spinal manipulation, two laterally spaced apart rods are connected to the pedicle screws whereby each rod extends along the spine with the object of the thus installed rods being maintenance of the disposition of the vertebrae as set by the surgeon's manipulation of the spine. This approach often reduces but fails to eliminate the spondylolisthesis aside from requiring a fair degree of skill from the surgeon.

A second known approach to addressing spondylolisthesis involves use of pedicle screws in combination with a posterior lumbar interbody fusion (PLIF) device. This approach is normally used when the intervertebral disc has been compromised such that there is need to restore foraminal height. A PLIF device of desired height but typically of small lateral and anterior-posterior extent is used. As the name suggests, the PLIF device is inserted by the surgeon from the posterior side of the patient with the inserted PLIF device not being held in place in the intervertebral space by pins or screws. Pedicle screws are then brought into use, as described above, with the surgeon carrying out his or her spondylolisthesis addressing manipulation before the rods are connected to the pedicle screws to maintain the disposition of the vertebrae as set by the surgeon's manipulation. In common with the first approach, this second approach often reduces but fails to eliminate the spondylolisthesis aside from requiring a fair degree of skill from the surgeon.

A third known approach to addressing spondylolisthesis involves use of an anterior lumbar interbody fusion (ALIF) device and perhaps also pedicle screws. In common with the second approach, this approach is normally used when the intervertebral disc has been compromised such that there is need to restore foraminal height. An ALIF device of desired height is inserted into the intervertebral space from the anterior side of the patient. The surgeon then manipulates the spine to address the spondylolisthesis. When the desired relative disposition of vertebrae has been achieved by manipulation, the surgeon may hold the ALIF device in place by pinning or screwing the ALIF device to the adjacent vertebrae. Pedicle screws may also be used to maintain the disposition of the vertebrae as set by the surgeon's manipulation; pedicle screws are typically used where the ALIF device is not pinned or screwed to adjacent vertebrae. In common with the first and second approaches, this third approach often reduces but fails to eliminate the spondylolisthesis aside from requiring a fair degree of skill from the surgeon.

A fourth known approach to addressing spondylolisthesis is a combined of anterior and posterior procedures. In common with the second and third approaches, this approach is normally used when the intervertebral disc has been compromised such that there is need to restore foraminal height. An ALIF device of desired height is inserted into the intervertebral space from the anterior side of the patient. The ALIF device is fixed to the inferior vertebra only of the adjacent vertebra. This provides initial correction of the spondylolisthesis as well as restoring foraminal height. The patient is then turned over to gain access to the posterior side of the patient. Pedicle screws are then put in place, as described above according to the first approach, while the surgeon pulls the spine to thereby slide the superior vertebra over the ALIF device to provide further correction of the spondylolisthesis. Although this approach demands a lower level of skill from the surgeon than the previous approaches, it is not always possible to slide the superior vertebra readily over the ALIF device to achieve the desired correction.

The present inventors have become appreciative of shortcomings of known procedures for correcting spondylolisthesis, such as the shortcomings mentioned above. The present invention has been devised in light of the inventors' appreciation of such shortcomings. It is therefore an object for the present invention to provide an improved intervertebral fusion device. It is a further object for the present invention to provide a method of installing an improved intervertebral fusion device.

STATEMENT OF INVENTION

According to a first aspect of the present invention there is provided an intervertebral fusion device comprising:

an endplate configured to be received in an intervertebral space defined between first and second vertebrae, the endplate having a leading end and a trailing end;

a core component configured to be received in the intervertebral space, the core component having a leading end and a trailing end; and at least one ratchet, each at least one ratchet comprising a pawl and a linear rack defining plural recesses, the pawl comprised in one of the core component and the endplate, the linear rack comprised in the other of the core component and the endplate, wherein the core component and the endplate are configured to engage with each other by disposing the leading end of the core component adjacent the trailing end of the endplate and then moving the core component relative to the endplate in a direction of insertion such that the leading end of the core component moves towards the leading end of the endplate and extent of overlap of the core component and the endplate increases, the plural recesses of the linear rack extend in the direction of insertion and from near or at one of the leading end and the trailing end of the other of the core component and the endplate towards the other of the leading end and the trailing end of the other of the core component and the endplate, the plural recesses extending by no more than 60% of a distance between the leading end and the trailing end, and the at least one ratchet is configured such that the pawl starts to inter-engage with the plural recesses of the linear rack as the core component is moved further relative to the endplate in the direction of insertion and such that the pawl progresses along the plural recesses with further relative movement of the core component until the core component and the endplate have a desired extent of overlap.

The intervertebral fusion device comprises an endplate and a core component. Each of the endplate and the core component has a leading end and a trailing end.

Each of the endplate and the core component is configured to be received in an intervertebral space defined between first and second vertebrae. As described further below, the endplate may be inserted into the intervertebral space first and then the core component may be inserted into the intervertebral space.

Alternatively, the endplate and the core component may be inserted together into the intervertebral space. Regardless of how the endplate and core component are inserted into the intervertebral space, the leading end of the endplate is received in the intervertebral space first of the leading and trailing ends of the endplate. Also, the leading end of the core component is received in the intervertebral space first of the leading and trailing ends of the core component.

The intervertebral fusion device further comprises at least one ratchet. Each at least one ratchet comprises a pawl and a linear rack defining plural recesses. The pawl is comprised in one of the core component and the endplate, and the linear rack is comprised in the other of the core component and the endplate. As described further below, the pawl may be integrally formed with the one of the core component and the endplate, and the linear rack may be integrally formed with the other of the core component and the endplate.

The core component and the endplate are configured to engage with each other by way of structures described below. The core component and the endplate are structured such that they are brought into engagement by disposing the leading end of the core component adjacent the trailing end of the endplate. Then the core component is moved relative to the endplate in a direction of insertion such that the leading end of the core component moves towards the leading end of the endplate whereby extent of overlap of the core component and the endplate progressively increases. As described further below, the core component and the endplate may be brought into engagement with each other, such as partial engagement, outside the intervertebral space and before the intervertebral fusion device is inserted into the intervertebral space. Alternatively, the endplate may be inserted into the intervertebral space and then the core component may be inserted into the intervertebral space and such that the core component is brought into engagement with the endplate.

The plural recesses of the linear rack extend in the direction of insertion and from near or at one of the leading end and the trailing end of the other of the core component and the endplate. The plural recesses extend towards the other of the leading end and the trailing end of the other of the core component and the endplate. The plural recesses extend by no more than 60% of a distance between the leading end and the trailing end of the other of the core component and the endplate. In forms of the invention, the plural recesses may extend by no more than 50% of a distance between the leading end and the trailing end of the other of the core component and the endplate. The at least one ratchet is configured such that the pawl starts to inter-engage with the plural recesses of the linear rack as the core component is moved further relative to the endplate in the direction of insertion. The pawl progresses along the plural recesses with further movement of the core component until the core component and the endplate have a desired extent of overlap.

Moving the core component such that the core component and the endplate have a desired extent of overlap, such as in registration with each other, may involve application of considerable force to the core component. It may be in the interests of the patient's health not to apply considerable force in an uncontrolled manner.

Having the plural recesses of the linear rack extend by no more than 60% of a distance between the leading end and the trailing end of the other of the core component and the endplate may mean that the pawl does not start to inter-engage with the plural recesses until the core component and endplate overlap by at least 40%. Force may be less likely to be applied to anatomy during this first stage of engagement of the core component with the endplate whereby there is less need to apply force in a controlled manner. Having the at least one ratchet not being operative during an initial stage of engagement of the core component and the endplate may provide for ease of their initial engagement. Having the plural recesses of the linear rack extend by no more than 60% of a distance between the leading end and the trailing end of the other of the core component and the endplate may provide for an appropriate balance between ease of initial engagement of the core component and the endplate and operation of the at least one ratchet during subsequent engagement of the core component and the endplate. In certain applications, having the plural recesses extend by no more than 50% of a distance between the leading end and the trailing end of the other of the core component and the endplate may provide for an appropriate such balance.

The plural recesses of the linear rack may extend by at least 20% of a distance between the leading end and the trailing end of the other of the core component. Having extension of the plural recesses by at least 20% of the distance may provide for application of force in a controlled manner in a wide range of applications. Having extension of the plural recesses by at least 30% of the distance has been found to be advantageous in certain applications, such as where a relatively wide range of spondylolisthesis may be corrected.

When the pawl inter-engages with the plural recesses during a subsequent second stage of engagement of the core component with the endplate, force may be applied to the core component step-by-step as the pawl progresses along the linear rack to increase the extent of overlap between the core component and the endplate and in a controlled manner. Force may be applied until the core component and the endplate have a desired extent of overlap, such as when the core component and the endplate are in registration with each other. During this second stage of engagement, force is more likely to be applied to anatomy directly and/or indirectly by way of the intervertebral fusion device. Application of considerable force may be of particular concern where spondylolisthesis is being corrected because of the need to apply sufficient force to move the first and second vertebrae relative to each other. Nevertheless, the present invention reduces the likelihood of undue force being applied to anatomy even when spondylolisthesis is not being corrected.

The intervertebral fusion device may comprise first and second ratchets. Each of the first and second ratchets may comprise a pawl and a linear rack defining plural recesses. The first and second ratchets may be spaced apart from each other in a transverse direction, i.e. in a direction orthogonal to the direction of insertion and to a direction of separation of the endplate and the core component when the intervertebral fusion device has been assembled. The linear racks of the first and second ratchets may therefore be spaced apart from each other in the transverse direction. Furthermore, the linear racks of the first and second ratchets may be substantially parallel to each other.

The pawl may comprise a finger which defines at least one protrusion at a distal end thereof. The finger may be attached at its proximal end at or near one of the leading end and the trailing end of the one of the core component and the endplate. The finger may extend in the direction of insertion towards the other of the leading end and the trailing end. More specifically, the distal end of the finger may be at or near the other of the leading end and the trailing end.

Where the intervertebral fusion device comprises first and second ratchets, the fingers may be spaced apart from each other in the transverse direction. Furthermore, the fingers may be substantially parallel to each other.

The finger may define plural protrusions, such as two protrusions, towards a distal end thereof. Having a finger which defines plural protrusions may provide for improved stability of inter-engagement of pawl and linear rack. The finger may define a first number of protrusions and the linear rack may define a second number of recesses, the second number being greater than the first number.

In one form, the plural recesses of the linear rack may extend from near or at the trailing end of the other of the core component and the endplate towards the leading end of the other of the core component and the endplate. Where the pawl comprises a finger, the finger may be attached at or near the leading end of the one of the core component and the endplate. For example, the plural recesses of the linear rack may extend from near or at the trailing end of the core component and the finger may be attached at or near the leading end of the endplate.

Where the intervertebral fusion device is being used to correct spondylolisthesis, the endplate may be a superior endplate or an inferior endplate. In use, the superior or inferior endplate may be inserted into the intervertebral space and may be attached to the adjacent vertebra. Then the core component may be inserted into the intervertebral space in engagement with the superior or inferior endplate and force applied as the extent of overlap of the core component and the superior or inferior endplate increases during correction of spondylolisthesis. Where the endplate is an inferior endplate, the linear rack may be comprised in the core component. Alternatively, and where the endplate is a superior endplate, the linear rack may be comprised in the superior endplate.

The intervertebral fusion device may comprise first and second endplates and the core component may be received between the first and second endplates when the core component is inserted into the intervertebral space. Alternatively, the intervertebral fusion device may comprise first and second endplates, and the second endplate may be comprised in and integrally formed with the core component. The first endplate may be placed in the intervertebral space and then the core component with its integral second endplate may be inserted into the intervertebral space and brought into engagement with the first endplate. Where spondylolisthesis is being corrected and where the second endplate is comprised in and integrally formed with the core component, such a configuration of intervertebral fusion device may be particularly suited to anterior lumbar interbody fusion procedures whereby the intervertebral fusion device may be an anterior lumbar interbody fusion (ALIF) device.

Where the intervertebral fusion device comprises first endplate, such as a superior endplate and a second endplate, such as an inferior endplate, which are components apart from the core component, the pawl and the linear track may be comprised in the core component and one of the first and second endplates. In one form, there may be no ratchet comprised in the core component and the other of the first and second endplates. More specifically, the core component and the other of the first and second endplates may be locked to each other by way of at least one protrusion bearing finger and corresponding single recess, as described further below. In another form, there may be at least one ratchet, such as first and second ratchets, comprised in the core component and the other of the first and second endplates. Movement of the core component relative to each of the first and second endplates may thus be regulated by the at least one ratchet comprised in the core component and the one of the first and second endplates, and by the at least one ratchet comprised in the core component and the other of the first and second endplates.

Further embodiments of the first aspect of the present invention may comprise one or more features of any of the further aspects of the present invention described below.

According to a second aspect of the present invention, there is provided a method of installing an intervertebral fusion device in an intervertebral space defined between first and second vertebrae, the intervertebral fusion device comprising an endplate having a leading end and a trailing end, a core component having a leading end and a trailing end, and at least one ratchet, each at least one ratchet comprising a pawl and a linear rack defining plural recesses, the pawl comprised in one of the core component and the endplate, the linear rack comprised in the other of the core component and the endplate, the plural recesses extending in a direction of insertion of the intervertebral fusion device into the intervertebral space and from near or at one of the leading end and the trailing end of the other of the core component and the endplate towards the other of the leading end and the trailing end of the other of the core component and the endplate, the plural recesses extending by no more than 60% of a distance between the leading end and the trailing end, the method comprising:

a) disposing the leading end of the core component adjacent the trailing end of the endplate;

b) bringing the core component into engagement with the endplate by moving the core component relative to the endplate in the direction of insertion such that the leading end of the core component moves towards the leading end of the endplate and extent of overlap of the core component and the endplate increases;

c) further moving the core component relative to the endplate in the direction of insertion whereby the pawl starts to inter-engage with the plural recesses of the linear rack and such that the pawl progresses along the plural recesses with further relative movement of the core component until the core component and the endplate have a desired extent of overlap; and d) installing the endplate and the core component in the intervertebral space.

The step of installing the endplate and the core component in the intervertebral space may be carried out after steps a) to c) such that the intervertebral fusion device is assembled before insertion into the intervertebral space. Alternatively, the step of installing the endplate and the core component in the intervertebral space may be carried out after steps a) and b) and before step c) such that the endplate and the core component are inserted together into the intervertebral space but before the at least one ratchet become operative. Step c) may then be carries when the endplate and the core component are in-situ in the intervertebral space. Alternatively, the step of installing the endplate and the core component in the intervertebral space may be carried out before steps a) to c) whereby the endplate only of the endplate and the core component is installed in the intervertebral space and the core component is installed in the intervertebral space by carrying out steps a) to c).

Further embodiments of the second aspect of the present invention may comprise one or more features of the first aspect of the present invention.

According to a first further aspect of the present invention there is provided an anterior lumbar interbody fusion device receivable in an intervertebral space between first and second vertebrae, the anterior lumbar interbody fusion device comprising:

a superior component having a superior component top side and a superior component bottom side, the superior component configured to be received in the intervertebral space whereby the superior component top side abuts against the first vertebra;

an inferior component having an inferior component top side and an inferior component bottom side, the inferior component configured to be received in the intervertebral space whereby the inferior component bottom side abuts against the second vertebra, the superior component bottom side and the inferior component top side opposing each other when the superior and inferior components are received in the intervertebral space; and a locking mechanism, wherein the superior and inferior components inter-engage with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction orthogonal to the anterior-posterior direction and to the direction of separation, each of: the at least a part of one of the superior and inferior components; and the other of the superior and inferior components is configured to engage with its respective vertebra whereby force is coupled between it and its respective vertebra, and the locking mechanism allows for movement of the at least a part of one of the superior and inferior components in the anterior-posterior direction which increases an extent of overlap of the at least a part of one of the superior and inferior components and the other of the superior and inferior components and presents resistance to movement of the at least a part of one of the superior and inferior components in the anterior-posterior direction which decreases an extent of overlap of the at least a part of one of the superior and inferior components and the other of the superior and inferior components.

The anterior lumbar interbody fusion device, which is commonly known as an ALIF device, comprises a superior component (which constitutes a superior endplate), an inferior component (which constitutes an inferior endplate) and a locking mechanism. The anterior lumbar interbody fusion device is introduced into a patient's intervertebral space from the anterior side of the patient. As described further below, the locking mechanism may in part be integrally formed with one of the superior and inferior components and more specifically with the other of the superior and inferior components. The anterior lumbar interbody fusion device is receivable in an intervertebral space between first and second vertebrae.

The superior component has a superior component top side and a superior component bottom side. The superior component is configured to be received in the intervertebral space whereby the superior component top side abuts against the first vertebra. The inferior component has an inferior component top side and an inferior component bottom side. The inferior component is configured to be received in the intervertebral space whereby the inferior component bottom side abuts against the second vertebra. The superior component bottom side and the inferior component top side oppose each other when the superior and inferior components are received in the intervertebral space.

The superior and inferior components inter-engage with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction, i.e. a transverse direction, orthogonal to the anterior-posterior direction and to the direction of separation. The at least a part of one of the superior and inferior components may comprise a respective one of at least a part of the superior component top side and at least a part of the inferior component bottom side.

Each of the at least a part of one of the superior and inferior components and the other of the superior and inferior components is configured to engage with its respective vertebra whereby force is coupled between it and its respective vertebra. Each of the at least a part of one of the superior and inferior components and the other of the superior and inferior components may be configured to inter-engage with its respective vertebra. Each of the at least a part of one of the superior and inferior components and the other of the superior and inferior components may be configured to engage by being shaped to abut against an aspect of the respective vertebra facing in the anterior-posterior direction.

Each of the at least a part of one of the superior and inferior components and the other of the superior and inferior components may be configured by way of teeth protruding from it. The teeth may inter-engage with the respective vertebra whereby force applied to the component is coupled to the vertebra and vice-versa.

Alternatively or in addition, each of the at least a part of one of the superior and inferior components and the other of the superior and inferior components may define at its anterior end at least one aperture for receiving a fixing member for fixing to a respective one of the first and second vertebrae. On reception of the superior and inferior components in the intervertebral space, each of the at least a part of one of the superior and inferior components and the other of the superior and inferior components is fixed to its respective one of the first and second vertebrae.

Constrained movement in the anterior-posterior direction of the at least a part of one of the superior and inferior components and the other of the superior and inferior components relative to each other enable the at least a part of one of the superior and inferior components and the other of the superior and inferior components to be misaligned with each other in the anterior-posterior direction to reflect the spondylolisthesis to be corrected.

The locking mechanism allows for movement of the at least a part of one of the superior and inferior components in the anterior-posterior direction that increases an extent of overlap of the at least a part of one of the superior and inferior components and the other of the superior and inferior components, i.e. a first anterior-posterior direction. Increase in the extent of overlap may decrease an extent of spondylolisthesis and may be achieved by the surgeon's action to decrease the extent of spondylolisthesis. Furthermore, the locking mechanism presents resistance to movement of the at least a part of one of the superior and inferior components in the anterior-posterior direction that decreases an extent of overlap of the at least a part of one of the superior and inferior components and the other of the superior and inferior components, i.e. a second anterior-posterior direction opposite the first anterior-posterior direction. The locking mechanism may thus present resistance to a decrease in extent of overlap and hence increase in extent of spondylolisthesis, such as when there is a pause in the surgeon taking action to decrease the extent of spondylolisthesis.

The superior component may abut against the first vertebra only of the first and second vertebrae. The inferior component may abut against the second vertebra only of the first and second vertebrae.

Spondylolisthesis usually involves the first vertebra, i.e. the upper vertebra, being displaced in the anterior direction relative to the second vertebra, i.e. the lower vertebra. Therefore, inter-engagement between superior and inferior components may be such that at least a part of the superior component is constrained to move in an anterior-posterior direction relative to the inferior component. In addition, inter-engagement between superior and inferior components may be such that resistance is presented to movement of the at least a part of the superior component relative to the inferior component in each of a direction of separation of the superior and inferior components and a direction orthogonal to the anterior-posterior direction and to the direction of separation. Furthermore, the locking mechanism may allow for movement of the at least a part of the superior component in the anterior-posterior direction which increases an extent of overlap of the at least a part of the superior component and the inferior component and presents resistance to movement of the at least a part of the superior component in the anterior-posterior direction which decreases an extent of overlap of the at least a part of the superior component and the inferior component.

The at least a part of one of the superior and inferior components may be shaped at its anterior end to abut against an anterior aspect of the respective one of the first and second vertebrae. Alternatively or in addition, the other of the superior and inferior components may be shaped at its anterior end to abut against an anterior aspect of the respective one of the first and second vertebrae. The component may be shaped by comprising a lug which extends from an anterior end of a main part of the component, the lug being at an angle to the main part of the component. The lug may abut against the anterior aspect of the respective vertebra when the component is received in the intervertebral space whereby force may be exerted against the vertebra to correct spondylolisthesis. The at least one aperture may be defined in the lug.

According to a first embodiment of the anterior lumbar interbody fusion device, the superior and inferior components may inter-engage with each other whereby: the superior and inferior components are constrained to move in an anterior-posterior direction relative to each other; and resistance is presented to movement of the superior and inferior components relative to each other in each of a direction of separation of the superior and inferior components and a direction orthogonal to the anterior-posterior direction and to the direction of separation. Likewise, each of the superior and inferior components may be configured to engage with its respective vertebra whereby force is coupled between it and its respective vertebra. More specifically, each of the superior and inferior components may define at its anterior end the at least one aperture for receiving a fixing member for fixing to a respective one of the first and second vertebrae. Also, the locking mechanism may allow for relative movement of the superior and inferior components in the anterior-posterior direction which increases an extent of overlap of the superior and inferior components and may present resistance to relative movement of the superior and inferior components in the anterior-posterior direction which decreases an extent of overlap of the superior and inferior components. The superior and inferior components may thus move relative to each other rather than a part of one of the superior and inferior components moving relative to the other of the superior and inferior components.

The superior and inferior components may inter-engage directly with each other, i.e. without an intervening component. Furthermore, each of the superior and inferior components may be unitary and more specifically may be integrally formed.

The superior component may define a superior component profile and the inferior component may define an inferior component profile, the superior and inferior component profiles inter-engaging with each other. More specifically, the superior and inferior component profiles may be configured for linear translation of one profile in relation to the other to thereby provide for movement in the anterior-posterior direction. Furthermore, the superior and inferior component profiles may be configured to restrict, and more specifically substantially prevent, relative movement of the superior and inferior components in a transverse direction. In addition, the superior and inferior component profiles may be configured to restrict, and more specifically substantially prevent more than limited, relative movement of the superior and inferior components in a direction of separation of the superior and inferior components, i.e. in a direction of separation of the first and second vertebrae.

One of the superior and inferior component profiles may define a channel which extends in the anterior-posterior direction and the other of the superior and inferior component profiles may define a formation which is received in and travels along the channel. More specifically, the inferior component profile may define the channel.

In a first form, the formation defined by the other of the superior and inferior component profiles may have the form of a protrusion, such as a cylindrical protrusion, which extends in the transverse direction. The protrusion may travel along the channel to change an extent of overlap of the superior and inferior components. Furthermore, the superior and inferior components may be configured such that the protrusion is rotatable in the channel whereby an inclination of the superior and inferior components to each other may be changed. More specifically, the protrusion may be disposed towards a posterior end of the other of the superior and inferior component profiles to thereby present a barrier to movement apart of the superior and inferior components towards their posterior ends whilst allowing for moving apart of the superior and inferior components at their anterior ends by virtue of rotation. As described further below, such a configuration may allow for use of a core component to determine angulation of the superior and inferior components to each other.

In a second form, the formation defined by the other of the superior and inferior component profiles may have the form of an elongate protrusion which extends in the anterior-posterior direction. The elongate protrusion may be slidably received in the channel to provide for change in extent of overlap of the superior and inferior components whilst presenting a barrier to separation of the superior and inferior components.

In each of the first and second forms, the superior component may define first and second superior component profiles which are spaced apart in the transverse direction and the inferior component may define first and second inferior component profiles which are spaced apart in the transverse direction. The first superior component profile and the first inferior component profile may inter-engage with each other and the second superior component profile and the second inferior component profile may inter-engage with each other to thereby present resistance and more specifically a barrier to relative movement of the superior and inferior components in the transverse direction.

The first and second superior component profiles may be towards a respective transverse side of the superior component and the first and second inferior component profiles may be towards a respective transverse side of the inferior component.

Each of the first and second inferior component profiles may respectively define first and second channels, the first and second channels facing each other. Furthermore, each of the first and second superior component profiles may respectively define first and second formations, the first formation being slidably received in the first channel and the second formation being slidably received in the second channel.

In an embodiment, the anterior lumbar interbody fusion device may lack the core component described below. In this embodiment, there may be no component, such as a core component, between the superior and inferior components.

Furthermore, according to this embodiment the superior component top side and the superior component bottom side may lie in substantially parallel planes and the inferior component bottom side and the inferior component top side may lie in substantially parallel planes whereby there is substantially no inclination between the superior and inferior components when they are installed in the intervertebral space.

Alternatively according to this embodiment, at least one of: the superior component top side and the superior component bottom side may be inclined to each other; and the inferior component bottom side and the inferior component top side may be inclined to each other. At least one of the superior and inferior components may therefore have the form of a wedge. Furthermore, an upper side and a lower side of the component may not meet at an acute angle whereby the component has the form of a frustum of a wedge. Furthermore, the inclination may be such that the component is thicker towards the anterior side than towards the posterior side. In a form, only the superior component of the superior and inferior components may have the form of a wedge.

In a different embodiment, the anterior lumbar interbody fusion device may comprise a core component configured for insertion between the superior and inferior components whereby a separation between the superior and inferior components is determined when the anterior lumbar interbody fusion device is in the intervertebral space.

An upper side and a lower side of the core component may be inclined to each other. The core component may therefore have the form of a wedge. Furthermore, the upper side and a lower side may not meet at an acute angle whereby the core component has the form of a frustum of a wedge. An inclination of the inferior and superior components relative to each other may thus be determined by way of the core component further to a separation between the inferior and superior components. Extent of inclination of the inferior and superior components may be determined by selection from a plurality of core components having upper and lower sides of different inclinations. Such selection may be combined with selection from a plurality of core components having different heights.

Where the superior and inferior components do not inter-engage directly with each other, the core component may provide for inter-engagement between the superior and inferior components. The core component may therefore inter-engage with each of the superior and inferior components whereby the superior and inferior components inter-engage with each other.

Irrespective of whether or not the superior and inferior components inter-engage directly with each other, the superior component and the core component may be configured to inter-engage with each other to present resistance and more specifically substantially prevent movement apart of the superior component and the core component. Alternatively or in addition, the superior component and the core component may be configured to inter-engage with each other to present resistance and more specifically substantially prevent relative movement of the superior component and the core component in the transverse direction.

The superior and core components may define surface profiles which cooperate to provide inter-engagement of the superior and core components which presents resistance and more specifically substantially prevents movement apart of the superior and core components. In addition, the surface profiles may provide for sliding engagement of the superior and core components when the core component is moved in the anterior-posterior direction relative to the superior component and more specifically such that resistance and more specifically a barrier is presented to relative movement of the superior and core components in the transverse direction. The superior and core components may be brought first into sliding engagement to progressively increase an extent of overlap of the superior and core components. The cooperating surface profiles may be shaped such that inter-engagement involving presenting resistance to movement apart of the superior and core components occurs when the superior and core components are at least one of: substantially half overlapping; and nearing full overlap.

The cooperating surface profiles may be shaped to draw the superior and core components together. More specifically the cooperating surface profiles may define surfaces which are inclined to a plane in which the anterior-posterior direction and the transverse direction lie and which ride over each other as the core component moves in the posterior direction relative to the superior component.

The superior component may define at least one surface profile, and more specifically two surface profiles spaced apart in the transverse direction, towards each of a posterior end of the superior component and an anterior end of the superior component and the core component may define at least one surface profile, and more specifically two surface profiles spaced apart in the transverse direction, towards each of a posterior end of the core component and an anterior end of the core component. The profiles at the posterior ends of the superior and core components may cooperate with each other and the profiles at the anterior ends of the superior and core components may cooperate with each other.

The cooperating surface profiles may be shaped such that upon movement of the core component in the posterior direction the cooperating surface profiles abut whereby the superior component moves in the posterior direction with the core component. When the core and superior components are substantially fully overlapping, and perhaps also when the core and superior components are locked together by way of the second locking mechanism described below, the core and superior components may be moved together relative to the inferior component to reduce an extent of spondylolisthesis.

The anterior lumbar interbody fusion device may comprise a second locking mechanism which is operative to present resistance and more specifically a barrier to relative movement of the core and superior components in the anterior-posterior direction which decreases an extent of overlap of the core and superior components. More specifically, the second locking mechanism may be operative to present resistance only when the core and superior components are substantially fully overlapping. Therefore, the second locking mechanism may be disengaged before the core and superior components are substantially fully overlapping whereby relative movement of the core and superior components is not resisted and may be engaged when the core and superior components are substantially fully overlapping. The second locking mechanism may comprise a second locking mechanism first part comprised in and more specifically integrally formed with the core component and a second locking mechanism second part comprised in and more specifically integrally formed with the superior component.

The second locking mechanism may be brought into engagement by relative movement of the core and superior components and more specifically relative movement in the anterior-posterior direction. Relative movement in the anterior-posterior direction may be provided by slidable engagement between the core and superior components. Slidable engagement between the core and superior components may be provided by the surface profiles of the core and superior components, as described above.

One of the second locking mechanism first and second parts may comprise a first profile defined by the respective one of the core and superior components and the other of the second locking mechanism first and second parts may comprise a second profile movably mounted on the respective one of the core and superior components. The second profile may move to a position in which the second profile engages with the first profile.

One of the second locking mechanism first and second parts may comprise two first profiles which are spaced apart from each other in the transverse direction. Also, the other of the second locking mechanism first and second parts may comprise two second profiles which are spaced apart from each other in the transverse direction. The two first profiles and the two second profiles may be disposed in their respective components such that each of the two first profiles engages with a respective one of the two second profiles.

The first profile may be a recess. More specifically, the recess may be defined by the core component. The second profile may be a protrusion shaped to be received in the recess. More specifically, the protrusion may be comprised in the superior component. The second locking mechanism may be engaged when the second profile is received in the recess.

Where the second profile is a protrusion, the protrusion may extend from a sprung portion which urges the protrusion in an inter-engaging direction towards the recess. The sprung portion may be a cantilever spring with, more specifically, the protrusion extending from towards a distal end of the cantilever spring. The sprung portion may be straight or tapered. Tapering controls stiffness and hence extent of deflection. A cantilever sprung structure may be simpler and more compact than other means of providing spring bias. A more compact structure is desirable in an anterior lumbar interbody fusion device in which space is usually at a premium. The cantilever sprung structure may lie along the anterior-posterior direction whereby little space is occupied by the cantilever sprung structure in the transverse direction.

Where there are two second profiles in the form of a protrusion, each of the two protrusions may extend from a respective one of two sprung portions. The two protrusions may extend in opposite directions. Alternatively or in addition, the two sprung portions may be spaced apart from each other in the transverse direction. Furthermore, the two sprung portions may be located towards a line which bisects the respective one of the core and superior components and more specifically towards a bisecting line which extends in the anterior-posterior direction.

The locking mechanism, i.e. first locking mechanism rather than the second locking mechanism described immediately above, allows for movement of the at least a part of one of the superior and inferior components in the anterior-posterior direction which increases an extent of overlap of the at least a part of one of the superior and inferior components and the other of the superior and inferior components and presents resistance to movement of the at least a part of one of the superior and inferior components in the anterior-posterior direction which decreases an extent of overlap of the at least a part of one of the superior and inferior components and the other of the superior and inferior components.

More specifically, the first locking mechanism allows for movement of at least a part of the superior component in the anterior-posterior direction which increases an extent of overlap of the at least a part of the superior component and the inferior component and presents resistance to movement of the at least a part of the superior component in the anterior-posterior direction which decreases an extent of overlap of the at least a part of the superior component and the inferior component.

In a first embodiment of the first locking mechanism, the first locking mechanism may be of a form and function as described above for the second locking mechanism. For example, and in respect of finer features, the second locking mechanism may comprise: two transversely spaced apart cantilever springs on the core component or superior component with a protrusion extending from towards a distal end of each cantilever spring; and two transversely spaced apart recesses on the inferior component, each protrusion being received in a respective one of the two recesses when the first locking mechanism is engaged.

According to the first embodiment of the first locking mechanism, and where the anterior lumbar interbody fusion device comprises a core component, the core and superior components may be coupled together, such as by way of the second locking mechanism described above, whereby the core and superior components move together in the anterior-posterior direction relative to the inferior component. The two transversely spaced apart cantilever springs may therefore be on the core component whereby the superior component moves with the core component. Alternatively, and where the anterior lumbar interbody fusion device lacks a core component, the two transversely spaced apart cantilever springs may be on the superior component. The first locking mechanism may thus involve inter-engagement directly between the superior and inferior components.

As described above, correction of spondylolisthesis may involve the surgeon moving one vertebra progressively or perhaps even stage-by-stage in the anterior-posterior direction relative to the adjacent vertebra. It may therefore be advantageous for the anterior lumbar interbody fusion device to resist decrease in overlap of the superior and inferior components at each of plural different extents of overlap. For example, the surgeon may first increase overlap and hence reduce spondylolisthesis to an initial extent before pausing to further increase overlap and hence further reduce spondylolisthesis. To address this, the first locking mechanism may be configured to present resistance to movement of the at least a part of the superior component in the anterior-posterior direction which decreases an extent of overlap of the at least a part of the superior component and the inferior component at each of plural different extents of overlap.

A first profile of the first locking mechanism may define plural locking formations, and more specifically recesses, which are spaced apart along the anterior-posterior direction. A second profile of the first locking mechanism may be movably mounted on its respective component to engage with each of the plural locking formations. Furthermore, the plural locking formations and the second profile may have the form of a ratchet whereby movement in the posterior direction is allowed and movement in the anterior direction is resisted. As mentioned above, the first locking mechanism may be of a form and function as described above for the second locking mechanism. The first locking mechanism may therefore comprise one or more further features of the second locking mechanism apart from the plural locking formations.

In a second embodiment of the first locking mechanism, the first locking mechanism may comprise a driving member which engages with each of the core component and the inferior component, the driving member being user operable to urge the core component over the inferior component and to thereby increase an extent of overlap of the core and inferior components. In this embodiment, the anterior lumbar interbody fusion device comprises a core component along with the superior and inferior components.

The first locking mechanism of the second embodiment may further comprise a threaded profile, and more specifically a threaded bore, comprised in one of the core component and the inferior component, and more specifically comprised in the inferior component, and an aperture defined by the other of the core component and the inferior component, and more specifically defined by the core component. Furthermore, the driving member may be configured to be received through the aperture for threaded engagement with the threaded profile, a driving member profile, such as a shoulder, of the driving member abutting against a periphery of the aperture. Rotation of the driving member, such as by a surgeon, may cause the driving member to move along the threaded profile in the posterior direction while abutting against the periphery of the aperture to thereby urge the core component and inferior component together and increase their extent of overlap.

According to a second embodiment of the anterior lumbar interbody fusion device, one of the superior and inferior components may comprise first and second component parts, the first component part moving relative to the other of the superior and inferior components in the anterior-posterior direction to change an extent of overlap between the first component part and the other of the superior and inferior components. Furthermore, the first component part may move relative to the second component part whereby there is substantially no change in extent of overlap between the second component part and the other of the superior and inferior components.

The first and second component parts may be comprised in the superior component.

The first component part and the second component part may define cooperating profiles which allow for relative movement of the first and second component parts. One of the first and second component parts, and more specifically the second component part, may define a channel in which part of the other of the first and second component parts is slidably received. More specifically, one of the first and second component parts may define two channels which are spaced apart in the transverse direction and which oppose each other. Furthermore, the other of the first and second component parts may define first and second edges at opposite transverse sides which are each shaped to be slidably received in a respective one of the two channels.

The first and second component parts may engage with each other such that the first component part is adjacent and can therefore abut against a vertebra. For example, and where the first and second component parts are comprised in the superior component, the first component part may be on a side of the second component part oppositely directed to the inferior component bottom side.

The second embodiment of the anterior lumbar interbody fusion device may further comprise a core component. The first component part and the core component may be configured to mechanically couple with each other whereby movement of the core component is coupled to the first component part to cause movement of the first component relative to the second component part. Movement of the core component, such as by a surgeon, may move the first component part relative to the second component part whereby extent of overlap is changed.

The first component part and the core component may be configured to mechanically couple with each other by way of cooperating formations. The core component may define a first formation, such as a formation surface, and the first component part may define a second formation, such as a formation protrusion, the formation protrusion and formation surface being shaped and located such that the formation protrusion bears against the formation surface to thereby mechanically couple movement of the core component to the first component part.

As described above, the second component part may be between the first component part and the core component. The second component part may therefore define an elongate aperture through which the formation protrusion extends and along which the formation protrusion travels.

The first component part and the core component may be configured to mechanically couple with each other by way of two pairs of cooperating formations, the two pairs of cooperating formations being spaced apart from each other in the transverse direction.

The superior and inferior components may be mechanically coupled to each other to restrict their relative movement in the transverse direction and in the anterior-posterior direction. More specifically, the superior and inferior components may be mechanically coupled for their relative rotation, such as by way of a hinge, about a rotation axis towards the posterior end. The inclination of the superior and inferior components to each other may thus be changed to receive differently angled core components.

The superior and inferior components may be mechanically coupled for their relative rotation and for relative movement in the direction of spacing apart of the superior and inferior components, i.e. in a translation direction which is orthogonal to each of the anterior-posterior direction and the transverse direction. More specifically, the superior and inferior components may be mechanically coupled by a hinge pin received in an elongate recess which extends in the translation direction.

The locking mechanism for the second embodiment of the anterior lumbar interbody fusion device may be of the same shape and form as described above in respect of the second embodiment of first locking mechanism except as will now be described. The threaded profile may be comprised in the second component part of the superior component and the aperture may be defined by the core component. The driving member may therefore move along the threaded profile whilst bearing against and thereby moving the core component, with movement of the core component being coupled to the first component part. Otherwise, the locking mechanism for the second embodiment of the anterior lumbar interbody fusion device may comprise one or more features of the first locking mechanism.

The anterior lumbar interbody fusion device may have dimensions appropriate for use as such. The superior component may have a range of length by width from 20 mm by 20 mm to 50 mm by 50 mm. The superior component may have a range of height at the posterior end from 1 mm to 4 mm. The inferior component may have a range of length by width from 20 mm by 20 mm to 50 mm by 50 mm. The inferior component may have a range of height at the posterior end from 1 mm to 4 mm. The core component may have a range of length by width from 20 mm by 20 mm to 50 mm by 50 mm. The core component may have a range of height at the posterior end from 4 mm to 10 mm.

Each of the superior and inferior components may have the form of a plate, albeit a plate having structures thereon that provide for inter-engagement as described above, whereby each is thin relative to its length and width. At least one of the superior component top side and the inferior component bottom side may be shaped in the coronal or sagittal planes, for example domed, to enhance fit and contact with adjacent vertebrae.

At least one of the superior and inferior components and the core component may have at least one aperture extending therethrough in a direction of separation of the inferior and superior components. Such at least one aperture may provide for distribution of bone graft material and, more specifically, where the at least one aperture is in the superior or inferior component, the at least one aperture may allow passage for bone graft material to engage with the adjacent vertebra.

At least one of the core component, the superior component and the inferior component may be formed by the like of casting, moulding or printing. Alternatively, at least one of the core component, the superior component and the inferior component may be formed by the like of machining or stamping.

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK, carbon reinforced PEEK or UHMWPE (Ultra High Molecular Weight PolyEthylene). In forms of the invention, the core component may be formed by 3D printing whereby the core component has the form of a 3D lattice. The aforementioned materials may be used to form the core component by way of 3D printing.

References herein, and in respect of the first and second further aspects, to anterior or to anterior aspect are in respect of the patient. Thus, the anterior side or aspect is the front of the patient. Correspondingly, references herein to posterior or to posterior aspect are in respect of the patient. Thus, the posterior side or aspect is the back of the patient. The anterior and posterior aspects are therefore oppositely directed.

According to a second further aspect of the present invention there is provided a method of correcting spondylolisthesis with an anterior lumbar interbody fusion device, the anterior lumbar interbody fusion device being receivable in an intervertebral space between first and second vertebrae and comprising a superior component, an inferior component and a locking mechanism, the method comprising:

receiving the superior component in the intervertebral space, the superior component having a superior component top side and a superior component bottom side, the superior component top side abutting against the first vertebra;

receiving the inferior component in the intervertebral space, the inferior component having an inferior component top side and an inferior component bottom side, the inferior component bottom side abutting against the second vertebra, the superior component bottom side and the inferior component top side opposing each other when the superior and inferior components are received in the intervertebral space;

bringing the superior and inferior components into inter-engagement with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction orthogonal to the anterior-posterior direction and to the direction of separation, each of the at least a part of one of the superior and inferior components and the other of the superior and inferior components is configured to engage with its respective vertebra whereby force is coupled between it and its respective vertebra; and moving the at least a part of one of the superior and inferior components in the anterior-posterior direction which increases an extent of overlap of the at least a part of one of the superior and inferior components and the other of the superior and inferior components, the locking mechanism allowing said extent of overlap increasing movement but presenting resistance to movement of the at least a part of one of the superior and inferior components in the anterior-posterior direction which decreases an extent of overlap of the at least a part of one of the superior and inferior components and the other of the superior and inferior components.

Embodiments of the second further aspect of the present invention may comprise one or more features of the first further aspect of the present invention.

According to a third further aspect of the present invention there is provided an intervertebral fusion device comprising:

a superior component having a superior component top side and a superior component bottom side, the superior component being configured to be received in an intervertebral space between first and second vertebrae whereby the superior component top side abuts against the first vertebra;

an inferior component having an inferior component top side and an inferior component bottom side, the inferior component being configured to be received in the intervertebral space between the first and second vertebrae whereby the inferior component bottom side abuts against the second vertebra, the superior component bottom side and the inferior component top side opposing each other when the superior and inferior components are received in the intervertebral space; and a core component configured for insertion between the superior and inferior components whereby a separation between the superior and inferior components is determined when the intervertebral fusion device is in the intervertebral space, wherein the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component, the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component being placed in the intervertebral space such that the superior component top side faces the first vertebra or what might remain of a partially removed intervertebral disc. The inferior component has an inferior component top side and an inferior component bottom side with the inferior component being placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components as described below.

The core component is configured for insertion between the superior and inferior components. In use, the core component may be inserted between the superior and inferior components when the superior and inferior components have been placed in the intervertebral space, as described above. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height.

The core component comprises a first core formation and one of the inferior component top side and the superior component bottom side comprises a first component formation. The first core formation inter-engages with the first component formation to present a barrier to separation of the core component and the corresponding one of the inferior and superior components from each other during insertion of the core component. The barrier to separation may be presented in a separation direction that extends between the inferior and superior components. Inter-engagement of the first core formation with the first component formation may provide for and maintain proper relative location of the core component and the corresponding one of the inferior and superior components in the separation direction during insertion of the core component. An extent to which the corresponding one of the inferior and superior components may move away from the core component in the separation direction may thus be limited during insertion of the core.

The core component also comprises a core profile and the other of the inferior component top side and the superior component bottom side comprises a component profile. The core profile and the component profile cooperate with each other during insertion of the core component to thereby guide the core component. During insertion of the core component, there is no barrier to separation of the core component and the corresponding one of the inferior and superior components from each other. The lack of barrier means the corresponding one of the inferior and superior components may move away from and towards the core component during insertion of the core component. Allowing for such movement of the core component away from and towards the corresponding one of the inferior and superior components may provide for ease of initial insertion of the core component, such as by way of reduced insertion load, and may allow for the position of the corresponding one of the inferior and superior components to settle in relation to the core component as insertion progresses.

The core component also comprises a second core formation and the other of inferior component top side and the superior component bottom side comprises a second component formation. The second core formation inter-engages with the second component formation to present a barrier to separation of the core component and the corresponding one of the inferior and superior components from each other when the core component is fully received between the inferior and superior components. The corresponding one of the inferior and superior components and the core component are thus held in relation to each other when the core component is fully received between the inferior and superior components. The core component may be fully received between the inferior and superior components when the core component abuts against a posterior surface of at least one of the inferior and superior components. As described above, the core profile and the component profile may cooperate with each other during insertion of the core component to guide the core component. The lack of barrier allows for the position of the corresponding one of the inferior and superior components to settle in relation to the core component as insertion progresses. When the position of the corresponding one of the inferior and superior components has settled in relation to the core component and the core is fully inserted, the barrier presented by inter-engagement of the second core formation and the second component formation presents a barrier to separation of the core component and the corresponding one of the inferior and superior components from each other.

The first core formation may be an inferior core formation and the first component formation may be an inferior component formation comprised in the inferior component top side. The barrier to separation may therefore be presented in respect of the core component and the inferior component. Furthermore, the core profile may be a superior core profile and the component profile may be a superior component profile comprised in the superior component bottom side. The lack of barrier to separation may therefore be in respect of the core component and the superior component. Having the intervertebral fusion device configured in this fashion may mean that the inferior component and core component are held together by virtue of the barrier to separation to thereby provide a firm foundation on which the intervertebral fusion device is assembled by affording more freedom of movement to the superior component during insertion of the core component.

The core component may have an upper side and a lower side. When the core component is inserted between the inferior and superior components, the upper side may face the superior component bottom side and the lower side may face the inferior component top side. The upper side and the lower side of the core component may be inclined to each other. The core component may therefore have the form of a wedge. Having the superior component profile and the superior core profile cooperate with each other with there being no resistance to separation of the core component and the superior component from each other whilst the inferior core formation inter-engages with the inferior component formation allows a wedge-shaped core component to be inserted between the inferior and superior components.

The upper side and the lower side of the core component may not meet at an acute angle whereby the core component has the form of a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having upper and lower sides of different relative inclinations.

One of the inferior component formation and the inferior core formation may define a groove and the other of the inferior component formation and the inferior core formation may define an elongate protrusion, the elongate protrusion being shaped to be slidably received in the groove. The elongate protrusion may be a friction fit in the groove. The groove and the elongate protrusion may extend between anterior and posterior aspects of the intervertebral fusion device. The inferior component formation may define the groove and the inferior core formation may define the elongate protrusion. Inter-engagement of groove and elongate protrusion present the barrier to separation as the core is inserted.

The inferior core formation may extend along the core component from a location on the core component spaced apart from an edge of the core component which leads insertion of the core component between the inferior and superior components. For example, and where the core component is wedge-shaped, the inferior core formation may extend along the core component from a location on the core component spaced apart from the thinner edge of the core component. Having the inferior core formation extend along the core component from a location on the core component spaced apart from the thinner edge allows the edge to be inserted first between the inferior and superior components and for the core component to be moved in the separation direction, i.e. the direction extending between the inferior and superior components, during a first stage of insertion before the inferior core formation and the inferior component formation inter-engage during a second stage of insertion. Allowing for freedom of movement in the separation direction during the first stage of insertion provides for ease of initial insertion of core component. For example, the edge of the core component may be inserted between the inferior and superior components with no great precision of positioning before the core component is pressed down against the inferior component as the core component is inserted further.

A leading edge of the core component, for example the thinner edge when the core component is wedge shaped, may have rounded corners. Such a radius on each corner of the leading edge may provide for ease of insertion of the core component between the inferior and superior components.

The inferior core formation may extend along the core component between the anterior and posterior aspects of the core component. Alternatively, the inferior core formation may extend along the core component for less than the span of the core component between the anterior and posterior aspects. The inferior core formation may extend along the core component starting from a location spaced apart from the leading edge of the core component by at least a quarter and more specifically at least a third of a distance between the leading edge and the opposite edge of the core component. In a particular form, the location may be spaced apart from the leading edge by about half of the distance between the leading edge and the opposite edge of the core component. The inferior core formation may extend along the core component from the starting location to the opposite edge of the core component.

The inferior component may comprise a first inferior component formation and a second inferior component formation, the first and second inferior component formations being towards opposite edges of the inferior component and being spaced apart in a direction transverse to the direction of insertion of the core component between the inferior and superior components. The core component may be received between the first and second inferior component formations during insertion. The first and second inferior component formations may therefore oppose each other. The core component may have first and second lateral sides which each face in a direction orthogonal to a direction of insertion of the core component and to a direction of separation of the inferior and superior components, with the first and second lateral sides facing in opposite directions. A first inferior core formation may be on the first lateral side and a second inferior core formation may be on the second lateral side. The first inferior component formation and the first inferior core formation may cooperate and the second inferior component formation and the second inferior core formation may cooperate to limit movement of the core component relative to the inferior component in the transverse direction. More specifically, the inferior component formations and the inferior core formations may provide a snug fit for the core component in the transverse direction.

The superior component may comprise a first superior component profile and a second superior component profile, the first and second superior component profiles being towards opposite edges of the superior component and being spaced apart in a direction transverse to the direction of insertion of the core component between the inferior and superior components. The core component may be received between the first and second superior component profiles during insertion. The first and second superior component profiles may therefore oppose each other. A first superior core profile may be on the first lateral side of the core component and a second superior core profile may be on the second lateral side of the core component. The first superior component profile and the first superior core profile may cooperate and the second superior component profile and the second superior core profile may cooperate to limit movement of the core component relative to the superior component in the transverse direction. More specifically, the superior component profiles and the superior core profiles may provide a snug fit for the core component in the transverse direction. As described above, there may be no barrier presented to separation of the superior component and the core component from each other. The superior component may therefore rise and fall in relation to the core component as insertion of the core component is guided by the superior component profiles and the superior core profiles.

The inferior component may comprise an inferior component rear formation which extends along a posterior aspect of the inferior component in a direction transverse to the direction of insertion of the core component. The posterior aspect is opposite the edge at which the core component is first received upon insertion. The core component may comprise an inferior core rear formation which extends along an edge of the core component which is first received between the inferior and superior components during insertion of the core component. The inferior component rear formation and the inferior core rear formation may inter-engage when the core component is fully received between the inferior and superior components to present a barrier to separation of the core component and the inferior component from each other in the separation direction. A leading edge of the core component, i.e. the edge first received between the inferior and superior components during insertion, may thus be secured against lifting away from the inferior component when the core component is fully inserted.

When the core component is fully inserted between the inferior and superior components it may be desirable to maintain the core component against ejection from between the inferior and superior components, i.e. movement of the core component in an opposite direction to the direction of insertion. The intervertebral fusion device may therefore comprise a locking arrangement, a first locking part being comprised in the core component and a second locking part being comprised in the inferior component, the first and second locking parts inter-engaging to present a barrier to ejection of the core component from between the inferior and superior components. The first locking part may comprise a living hinge which defines a protrusion thereon and the second locking part may define an aperture. The living hinge may be urged by inherent spring bias in a direction of separation of the inferior and superior components and such that that the protrusion on the living hinge is received in the aperture of the second locking part.

The second component formation may be a superior component rear formation comprised in the superior component. The superior component rear formation may extend along a posterior aspect of the superior component in a direction transverse to the direction of insertion of the core component. The posterior aspect is opposite the edge at which the core component is first received upon insertion. The second core formation may be a superior core rear formation comprised in the core component. The superior core rear formation may extend along an edge of the core component which is first received between the inferior and superior components during insertion of the core component. As described above in respect of the second component formation and the second core formation, the superior component rear formation and the superior core rear formation inter-engage when the core component is fully inserted to present a barrier to separation of the core component and superior component. As described above, the superior component profile and the superior core profile cooperate with each other to present no resistance to separation of the core component and the superior component from each other in the separation direction during insertion of the core component. The superior component rear formation and the superior core rear formation thus present a barrier to separation when the core component is fully inserted, for example when the core component abuts against a posterior surface of at least one of the inferior and superior components.

The superior component rear formation and the superior core rear formation may be configured such that they start to engage when the core component is at least 80% and more specifically at least 90% inserted between the inferior and superior components. The superior component rear formation and the superior core rear formation may be configured by their extension away from the posterior aspect towards the anterior aspect.

The superior component rear formation may comprise a first protrusion and the superior core rear formation may comprise a second protrusion, the second protrusion being received on the core component side of the first protrusion when the core component is fully inserted. Furthermore, the superior component rear formation and the superior core rear formation may be shaped to draw the superior component and the core component progressively closer together during a last stage of insertion of the core component. As mentioned above, the superior component rear formation and the superior core rear formation may start to inter-engage when the core component is at least 80% inserted. Each of the first and second protrusions may define an inclined surface, the two inclined surfaces sliding over each other to draw the superior component and the core component progressively closer together.

The second component formation may be a superior component front formation comprised in the superior component. The superior component front formation may be towards an edge of the superior component at which the core component is first received upon insertion of the core component. The second core formation may be a superior core front formation comprised in the core component. The superior core front formation may be towards an edge of the core component opposite the edge first received between the inferior and superior components during insertion of the core component. The superior component front formation and the superior core front formation may inter-engage when the core component is fully inserted to present a barrier to separation of the core component and superior component in the separation direction. The superior component front formation and the superior core front formation may inter-engage and the superior component rear formation and the superior core rear formation may also inter-engage to present barriers to separation at opposite edges of the core component. The superior component front formation and the superior core front formation, and the superior component rear formation and the superior core rear formation may be operative to stop the superior component lifting or at least limit an extent to which the superior component can lift from the core component.

The superior component front formation may comprise a recess and the superior core rear formation may comprise a protrusion, the protrusion being received on the recess when the core component is fully inserted. Furthermore, the superior component front formation and the superior core front formation may be shaped to draw the superior component and the core component progressively closer together during a last stage of insertion of the core component. Each of the superior component front formation and the superior core front formation may define an inclined surface, the two inclined surfaces sliding over each other to draw the superior component and the core component progressively closer together. The superior component front formation and the superior core front formation may start to inter-engage with each other at a same extent of insertion of the core component as when the superior component rear formation and the superior core rear formation start to inter-engage with each other. Opposite edges of the core component are thus drawn towards the superior component simultaneously as the core component is inserted.

References herein, and in respect of the third and fourth further aspects, to anterior or to anterior aspect are to the anterior aspect of the intervertebral fusion device itself and not to the anterior aspect of the patient. The anterior aspect of the intervertebral fusion device itself therefore means the aspect at which the core component is inserted between the superior and inferior components. Correspondingly, references herein to posterior or to posterior aspect are to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. Such a less gentle insertion process may damage the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction. Each of the superior component, the inferior component and the core component may be integrally formed. The superior component and the inferior component may not engage with each other, other than by way of the core component.

Each of the inferior and superior components may have the form of a plate, albeit a plate having structures thereon that provide for mechanical engagement with the core component, whereby it is thin relative to its length and width. At least one of the superior component top side and the inferior component bottom side may be shaped in the coronal or sagittal planes, for example domed, to enhance fit and contact with the adjacent vertebrae. The coronal plane divides the body into dorsal and ventral (back and front, or posterior and anterior) portions. A direction may be said to be coronal if it lies on or is parallel to the coronal plane. A coronal direction may thus extend from one of the right and left of the body to the other of the right and left of the body.

At least one of the superior component top side and the inferior component bottom side may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP).

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK or carbon reinforced PEEK. In forms of the invention, the core component may be formed by 3D printing whereby the core component has the form of a 3D lattice. The aforementioned materials may be used to form the core component by way of 3D printing.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

According to a fourth further aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

- positioning the superior component and the inferior component relative to each other such that the superior component bottom side and the inferior component top side oppose each other;
- inserting the core component between the superior and inferior components whereby a separation between the superior and inferior components is determined; and
- disposing the intervertebral fusion device in the intervertebral space such that the superior component top side abuts against the first vertebra and the inferior component bottom side abuts against the second vertebra,
- wherein the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component,
- wherein the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and
- wherein the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Further embodiments of the fourth further aspect of the present invention may comprise one or more features of the third further aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 1A:
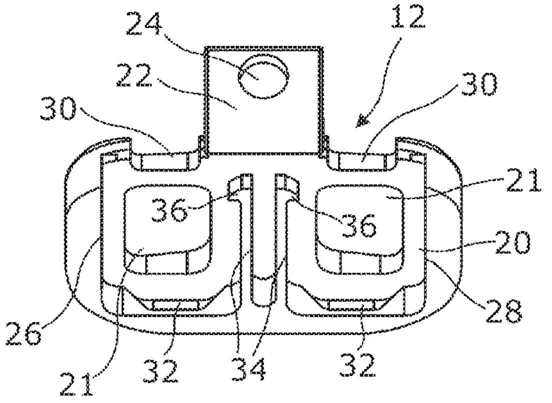
FIG. 1A is a perspective view from below of a superior component of a first embodiment of anterior lumbar interbody fusion device.

A first embodiment of anterior lumbar interbody fusion device 10 is shown in FIGS. 1A to 11. An anterior lumbar interbody fusion (ALIF) device is introduced into a patient's intervertebral space between first and second adjacent vertebrae from the anterior side of the patient. The first embodiment of anterior lumbar interbody fusion device 10 comprises a superior component 12 (which constitutes a superior endplate), a core component 14 and an inferior component 16 (which constitutes an inferior endplate). Perspective views of the superior component 12 from below and above are shown respectively in FIGS. 1A and 1B. Views of the core component 14 from above, one side and below are shown respectively in FIGS. 1C to 1E. Perspective views of the inferior component 16 from above and below are shown respectively in FIGS. 1F and 1G. FIG. 1H is a perspective view from above of the first embodiment of anterior lumbar interbody fusion device 10 when assembled and installed in an intervertebral space of a patient and before correction of spondylolisthesis. FIG. 1H shows the anterior lumbar interbody fusion device 10 before correction of a Grade 2 spondylolisthesis. FIG. 1I is a perspective view from above of the first embodiment of anterior lumbar interbody fusion device 10 when assembled and after correction of the spondylolisthesis.

Each of the superior component 12 and the inferior component 16 is generally of the form of a plate, albeit a plate having structures thereon and two spaced apart apertures therethrough. The core component 14 has the form of a frustum of a wedge. The anterior lumbar interbody fusion device 10 is assembled and installed in the intervertebral space first by insertion of the superior component 12 and the inferior component 16 into the intervertebral space with an insertion tool of known form and function. The insertion tool also holds the superior component 12 and the inferior component 16 within the intervertebral space. For example, a Prodisc® L inserter from Centinel Spine, Inc., 900 Airport Road, Suite 3A, West Chester, PA 19380, USA is used as the insertion tool after modification to take account of the offset of the vertebrae. The inserted superior and inferior components are fixed with screws to the lower or second vertebra. Alternatively, screw fixing of at least one of the inserted superior and inferior components and more typically of the superior component is deferred until after insertion of the core component between the superior and inferior components and correction of the spondylolisthesis. The insertion tool is then used to insert the core component 14 between the superior and inferior components 12, 16. On account of the offset of the superior and inferior components 12, 16 caused by the spondylolisthesis, the core component 14 inter-engages in the intervertebral space first with the superior component. Upon further insertion, the core component begins to slidably inter-engage with the inferior component. Following further insertion of the core and when the superior and core components 12, 14 are fully inter-engaged with each other they are then moved together in the posterior direction relative to the inferior component 16 such that the extent of overlap of the superior and inferior components 12, 16 increases until the superior component 12 is aligned with the upper or first vertebra. As mentioned above, the superior component 12 is fixed with a screw to the upper vertebra either during the procedure or upon conclusion of the procedure. At this stage in the procedure, the anterior lumbar interbody fusion device 10 has the disposition shown in FIG. 1H which reflects the extent of spondylolisthesis before correction. The surgeon then manipulates the patient to correct the spondylolisthesis with this involving further movement of the superior and core components 12, 14 together in the posterior direction relative to the inferior component 16 to increase the extent of overlap of the superior and inferior components until the spondylolisthesis is corrected. At this stage in the procedure, the anterior lumbar interbody fusion device 10 has the disposition shown in FIG. 1I. As will become clear from the following description, the anterior lumbar interbody fusion device 10 is configured to resist spondylolisthesis increasing movement of the superior and core components 12, 14 together in the anterior direction. Further description is provided below of form and function in respect of the like of inter-engagement of the superior and core components 12, 14, inter-engagement of the core and inferior components 14, 16, fixing of the superior and inferior components 12, 16 to vertebrae, and resistance to spondylolisthesis increasing movement of the superior and core components 12, 14 together in the anterior direction.

Figure 1B:
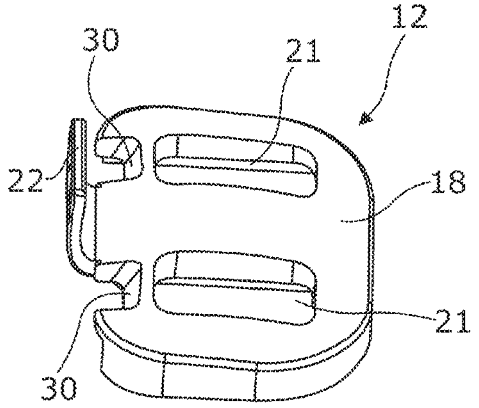
FIG. 1B is a perspective view from above of the superior component of FIG. 1A.

Turning now to FIGS. 1A and 1B, the superior component 12 is integrally formed from a metal or plastics material and has a superior component top side 18 and a superior component bottom side 20. The superior component 12 is of a size such that it can be received in the intervertebral space whereby the superior component top side 18 abuts against the upper vertebra. The superior component 12 defines two apertures 21 which extend therethrough and are spaced apart from each other in the transverse direction. The two apertures 21 allow for passage of bone graft material from inside the anterior lumbar interbody fusion device 10. The superior component 12 has an integrally formed superior lug 22 which extends from an anterior end of the superior component and substantially orthogonally to the superior component top side 18 such that the superior lug extends above the superior component top side. The superior lug 22 defines a superior lug aperture 24 extending therethrough. As described above, the surgeon aligns the superior component 12 with the upper vertebra and fixes the superior component 12 with a screw to the upper vertebra. Considering this latter part of the surgical procedure further, the superior component 12 is aligned with the upper vertebra by moving the superior component 12 together with the core component 14 in the posterior direction into the intervertebral space until the superior lug 22 abuts against the anterior aspect of the upper vertebra. The surgeon then drives the screw through the superior lug aperture 24 and into the upper vertebra to fix the superior component 12 to the upper vertebra. Alternatively, screw fixing is deferred until the spondylolisthesis has been corrected.

Considering FIG. 1A in particular, the superior component 12 defines integrally formed structures at the superior component bottom side 20. The structures comprise first and second straight walls 26, 28 which each extend up from the superior component bottom side 20 and away from the superior component top side 18. Each of the first and second walls 26, 28 is towards a respective transverse side of the superior component 12 such that the first and second walls are parallel and face each other. The first and second walls 26, 28 run in the anterior-posterior direction. As described further below, the first and second walls engage with sides of the core component 14 and guide movement of the core component relative to the superior component 12 as the core component is being brought into inter-engagement with the superior component.

The structures at the superior component bottom side 20 further comprise first and second anterior recesses 30 and first and second posterior recesses 32. The first and second anterior recesses 30 are defined in the anterior edge of the superior component 12 and such that they are spaced apart from each other in the transverse direction. As can be seen from FIG. 1B, the base of each of the first and second anterior recesses 30 is inclined to a plane in which the anterior-posterior direction and the transverse direction lie whereby the base of the recess slopes upwards away from the anterior side. As described further below, a sloped surface of a corresponding protrusion on the core component 14 rides over the sloped base of each anterior recess 30 to draw the core component and superior component together and into inter-engagement. The first and second posterior recesses 32 are defined in a respective one of aligned posterior walls near the posterior side of the superior component 12. The posterior walls extend in the transverse direction and up from the superior component bottom side 20. The first and second posterior recesses 32 are therefore spaced apart from each other in the transverse direction.

Each of the first and second posterior recesses 32 is elongate in the transverse direction and extends in the orthogonal direction up from the base of its posterior wall. Each of the first and second posterior recesses 32 is inclined to a plane in which the anterior-posterior direction and the transverse direction lie whereby the posterior recess is sloped between its leading edge and its base. As described further below, a sloped surface of a corresponding protrusion on the core component 14 rides over the sloped posterior recess 32 to draw the core component and superior component together and into inter-engagement.

The structures at the superior component bottom side 20 further comprise first and second superior cantilever spring structures 34. Each cantilever spring structure 34 comprises a cantilever spring member which extends at its proximal end from near the posterior end of the superior component 12 to near the anterior end of the superior component. A protrusion 36 extends in the transverse direction from towards a distal end of the cantilever spring member. The two cantilever spring members are substantially parallel and each of the cantilever spring members is substantially parallel with and facing a respective one of the first and second straight walls 26, 28. The first and second superior cantilever spring structures 34 are located on a respective side of a line which bisects the superior component 12 and which extends in the anterior-posterior direction whereby the first and second superior cantilever spring structures are spaced apart to a small extent from each other in the transverse direction.

Furthermore, the protrusions 36 project in opposite directions from their respective cantilever spring members towards their respective first and second straight walls 26, 28. As described further below, each of the protrusions 36 on the first and second superior cantilever spring structures 34 is received in a respective recess defined by the core component 14 to lock the superior component 12 and the core component together. The first and second superior cantilever spring structures 34 and the recesses on the core component constitute a second locking mechanism.

Figure 1C:
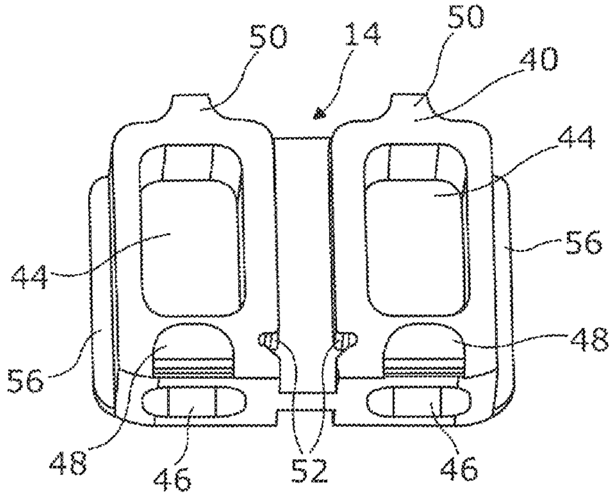
FIG. 1C is a view from above of a core component of the first embodiment of anterior lumbar interbody fusion device.
Figure 1D:
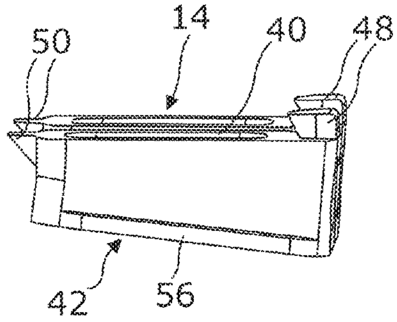
FIG. 1D is a view from a side of the core component of FIG. 1C.
Figure 1E:
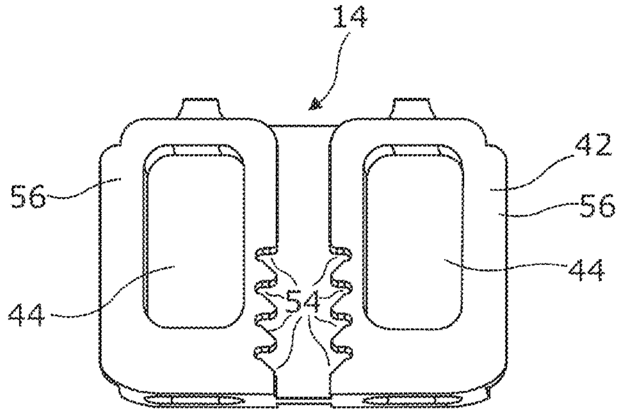
FIG. 1E is a view from below of the core component of FIG. 1C.

Turning now to FIGS. 1C to 1E, the core component 14 is integrally formed from a metal or plastics material and has an upper side 40 and a lower side 42. As can be seen from FIG. 1D, the upper side 40 and the lower side 42 are inclined to each other and do not meet at an acute angle whereby the core component 14 has the form of a frustum of a wedge with the thickest part of the wedge at the anterior side of the core component. The core component defines two bone graft material receiving spaces 44 which are spaced apart from each other in the transverse direction with each bone graft material receiving space extending from the upper side 40 to the lower side 42. Two spaced apart bone graft material receiving apertures 46 are defined in the anterior side of the core component 14 such that they are spaced apart from each other in the transverse direction. Each bone graft material receiving aperture 46 is in fluid communication with a respective one of the two bone graft material receiving spaces 44 whereby bone graft material can be introduced into the receiving space 44 by way of the bone graft material receiving aperture. When the superior component 12 and the core component 14 are installed in the intervertebral space, bone graft material held in the bone graft material receiving spaces 44 passes through the two apertures 21 in the superior component to thereby help provide for fusion with the adjacent vertebra. Likewise, bone graft material held in the bone graft material receiving spaces 44 passes through two apertures in the inferior component 16, which is described below.

The core component 14 defines integrally formed structures on each of the upper side 40 and the lower side 42. The structures on the upper side 40 of the core component 14 comprise first and second anterior protrusions 48 and first and second posterior protrusions 50. The first and second anterior protrusions 48 extend up from the upper surface and at the anterior edge of the core component 14 but within the anterior boundary and such that they are spaced apart from each other in the transverse direction. As can be seen from FIG. 1D, the posterior facing side of each of the first and second anterior protrusions 48 is inclined to a plane in which the anterior-posterior direction and the transverse direction lie whereby the base of the posterior facing side slopes up and away from the anterior side. The first and second posterior protrusions 50 extend from the posterior side of the core component 14 and such that an upper side of each posterior protrusion is an extension of and lies in the same plane as the upper surface 40. Furthermore, the first and second posterior protrusions 50 are spaced apart from each other in the transverse direction. Each of the first and second posterior protrusions 50 is defined by the extension of the upper side 40 which terminates in an elongate sharp edge and by a lower side of the protrusion which extends away from the elongate sharp edge to the posterior side of the core component 14. The lower side is inclined to a plane in which the anterior-posterior direction and the transverse direction lie whereby the lower side is sloped between the elongate sharp edge and the posterior side.

The structures on the upper side 40 of the core component 14 further comprise a first channel which extends between the anterior and posterior ends of the core component such that it bisects the core component. A recess 52 is defined in each of the opposing walls of the first channel and such that the recesses are in registration with each other and near the anterior end of the core component. Each recess 52 is shaped to receive a respective one of the protrusions 36 on the first and second superior cantilever spring structures 34.

The core component 14 is brought into inter-engagement with the superior component 12 by first fitting the posterior end of the core component between the anterior ends of the first and second straight walls 26, 28 of the superior component. The width of the core component 14 in the transverse direction and the spacing apart of the first and second straight walls 26, 28 is such that the core component is a snug fit between the first and second straight walls whilst allowing for sliding relative movement of the core and superior components. As the posterior end of the core component is fitted between anterior ends of the first and second straight walls 26, 28, the ends of the first and second superior cantilever spring structures 34 abut against respective curved edges of the first channel in the core component. The core component 14 is then slid in the posterior direction such that there is a progressive increase in an extent of overlap of the core and superior components as the posterior end of the core component moves towards the posterior end of the superior component. As the core component 14 is slid in the posterior direction, the ends of the first and second superior cantilever spring structures 34 travel along the curving together walls of the first channel whereby the ends of the first and second superior cantilever spring structures are pressed towards each other and thereby develop spring bias.

As the posterior end of the core component approaches the posterior end of the superior component, the elongate sharp edges of the first and second posterior protrusions 50 are received in their respective first and second posterior recesses 32. Further movement of the posterior end of the core component towards the posterior end of the superior component causes the sloped lower side of each of the first and second posterior protrusions 50 to ride up over the slope defined by a respective one of the first and second posterior recesses 32 whereby the posterior end of the core component and the posterior end of the superior component are drawn together. Furthermore, and as the posterior end of the core component approaches the posterior end of the superior component, the first and second anterior protrusions 48 are received in their respective first and second anterior recesses 30. Further movement of the posterior end of the core component towards the posterior end of the superior component causes the sloped posterior facing side of each of the first and second anterior protrusions 48 to ride up the sloped base of each of the first and second anterior recesses 30 whereby the anterior end of the core component and the anterior end of the superior component are drawn together.

When the posterior end of the core component is approaching full reception at the posterior end of the superior component, the protrusion 36 on each of the first and second superior cantilever spring structures 34 starts to be received in a respective one of the two recesses 52 defined in the opposing walls of the first channel in the core component. Each protrusion 36 is urged into its respective recess 52 by the spring bias of the respective one of the first and second superior cantilever spring structures 34. When the protrusions 36 are fully received in their respective recesses 52 upon full reception of the posterior end of the core component at the posterior end of the superior component, the spring bias of the first and second superior cantilever spring structures 34 presents resistance to ejection of the protrusions 36 from the recesses 52. Furthermore, each protrusion 36 and each recess 52 is shaped for movement of their surfaces over each other to allow for ease of reception of protrusion in recess as the core component moves in the posterior direction and for their surfaces to abut against each other to present a barrier against ejection of protrusion from recess upon application of force liable to move the core component in the opposite, anterior direction. The superior and core components 12, 14 are thus structured to present resistance to ejection of the core component in the anterior direction relative to the superior component when the anterior lumbar interbody fusion device 10 is in situ in the intervertebral space.

Referring now to FIG. 1E in particular, structures on the lower side 42 of the core component 14 comprise a second channel which extends between the anterior and posterior ends of the core component such that it bisects the core component. First and second sets of plural recesses 54 (each set of plural recesses constitutes a linear rack of a ratchet) are defined in each of the opposing walls of the second channel. The plural recesses 54 defined in each wall are equally spaced apart in the anterior-posterior direction. Also, the set of plural recesses 54 in one wall are in registration with the set of plural recesses 54 in the other wall such that each recess in one wall is in registration with a recess in the other wall. The plural recesses 54 in each wall are shaped to form a toothed rack which permits movement of a protrusion comprised in the inferior component 16 in the anterior direction only of the posterior and anterior directions. The structures on the lower side 42 of the core component 14 further comprise first and second ledges 56. Each ledge 56 projects in the transverse direction from a respective transverse side of the core component 14 and extends between the anterior and posterior sides of the core component. Each ledge 56 projects from its transverse side with one side of the ledge planar with and an extension of the lower side 42 of the core component whereby the ledge projects from an edge between the transverse side and the lower side 42 of the core component.

Figure 1F:
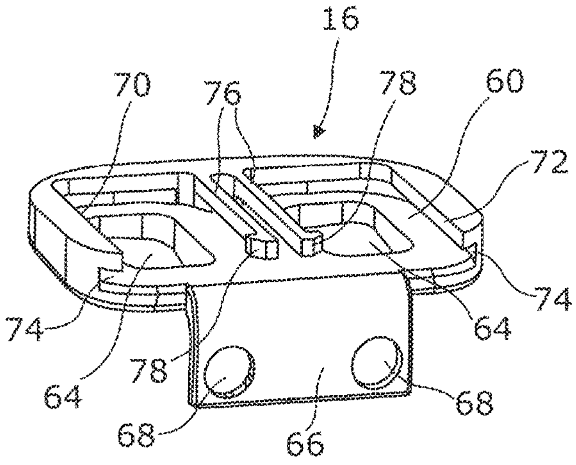
FIG. 1F is a perspective view from above of an inferior component of the first embodiment of anterior lumbar interbody fusion device.
Figure 1G:
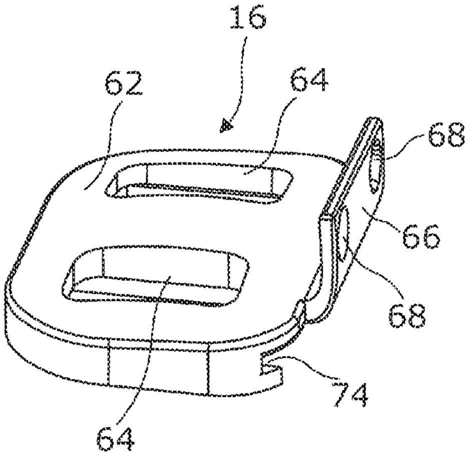
FIG. 1G is a perspective view from below of the inferior component of FIG. 1F.

Turning now to FIGS. 1F and 1G, the inferior component 16 is integrally formed from a metal or plastics material and has an inferior component top side 60 and an inferior component bottom side 62. The inferior component 16 is of a size such that it can be received in the intervertebral space whereby the inferior component bottom side 62 abuts against the lower vertebra. The inferior component 16 defines two apertures 64 which extend therethrough and are spaced apart from each other in the transverse direction. The two apertures 64 allow for passage of bone graft material from inside the anterior lumbar interbody fusion device 10. The inferior component 16 has an integrally formed inferior lug 66 which extends from an anterior end of the inferior component and substantially orthogonally to the inferior component bottom side 62 such that the inferior lug extends above the inferior component bottom side. The inferior lug 66 defines two inferior lug apertures 68 extending therethrough. The two inferior lug apertures 68 are spaced apart in the transverse direction. As described above, the surgeon aligns the inferior component 16 with the lower vertebra and fixes the inferior component 16 to the lower vertebra with screws. Screw fixing is done either when the superior and inferior components are first inserted into the intervertebral space or after correction of the spondylolisthesis. Considering this part of the surgical procedure further, the inferior component 16 is aligned with the lower vertebra by moving the inferior component 16 into the intervertebral space in the posterior direction until the inferior lug 66 abuts against the anterior aspect of the lower vertebra. The surgeon then drives a screw through each of the inferior lug apertures 68 and into the lower vertebra to fix the inferior component 16 to the lower vertebra.

Considering FIG. 1F in particular, the inferior component 16 defines integrally formed structures at the inferior component top side 60. The structures comprise first and second walls 70, 72 which each extend up from the inferior component top side 60 and away from the inferior component bottom side 62. Each of the first and second walls 70, 72 is towards a respective transverse side of the inferior component 16 such that the first and second walls are parallel and face each other. The first and second walls 70, 72 run in the anterior-posterior direction. Each of the first and second walls 70, 72 defines a channel 74 which extends along the length of the wall in the anterior-posterior direction.

The structures at the inferior component top side 60 yet further comprise first and second inferior cantilever spring structures 76 (which each constitute a pawl of a ratchet). Each inferior cantilever spring structure 76 comprises a cantilever spring member which extends at its proximal end from near the posterior end (which constitutes the leading end) of the inferior component 16 to near the anterior end (which constitutes the trailing end) of the inferior component. A protrusion 78 projects in the transverse direction from towards a distal end of the inferior cantilever spring member. The two inferior cantilever spring members are substantially parallel and each of the inferior cantilever spring members is substantially parallel with and facing a respective one of the first and second straight walls 70, 72. The first and second inferior cantilever spring structures 76 are located on a respective side of a line which bisects the inferior component 16 and which extends in the anterior-posterior direction whereby the first and second inferior cantilever spring structures are spaced apart to a small extent from each other in the transverse direction. Furthermore, the protrusions 78 project in opposite directions from their respective inferior cantilever spring members towards their respective first and second straight walls 70, 72. As described further below, each of the protrusions 78 on the first and second inferior cantilever spring structures 76 is received in a respective recess 54 defined by the core component 14 to lock the inferior component 16 and the core component together.

As described above, the surgical procedure involves inserting the superior and inferior components 12, 16 into the intervertebral space and inserting the core component 14 between the superior and inferior components with there being inter-engagement between core component and superior component and inter-engagement between core component and inferior component. Inter-engagement between inferior and core components 16, 14 involves the posterior end of the core component 14 being fitted between the anterior ends of the first and second walls 70, 72 of the inferior component 16 such that each ledge 56 is slidably received in a respective channel 74. As the posterior end of the core component 14 is fitted in this fashion, the ends of the first and second inferior cantilever spring structures 76 abut against respective curved edges of the second channel in the core component. The core component 14 is then slid in the posterior direction such that there is a progressive increase in an extent of overlap of the core and inferior components as the posterior end of the core component moves towards the posterior end of the inferior component.

As the core component 14 is slid in the posterior direction, the ends of the first and second inferior cantilever spring structures 76 travel along the curving together walls of the second channel whereby the ends of the first and second inferior cantilever spring structures are pressed towards each other and thereby develop spring bias.

As the core component 14 and inferior component 16 are approaching about fifty percent overlap with each other, the protrusion 78 on each of the first and second inferior cantilever spring structures 76 is received under spring bias in a first recess in a respective one of the first and second sets of plural recesses 54. As described above, the plural recesses 54 in each set of plural recesses are shaped to form a toothed rack which in view of the corresponding shape of the protrusion 78 permits movement of the protrusion relative to the toothed rack in the anterior direction only of the posterior and anterior directions. The two sets of plural recesses 54 and the first and second inferior cantilever spring structures 76 constitute the first locking mechanism (or ratchet). The surgeon can therefore cease applying force to reduce the extent of spondylolisthesis whereupon operation of the first locking mechanism presents resistance to movement of the core component in the posterior, spondylolisthesis increasing direction.

Figure 1H:
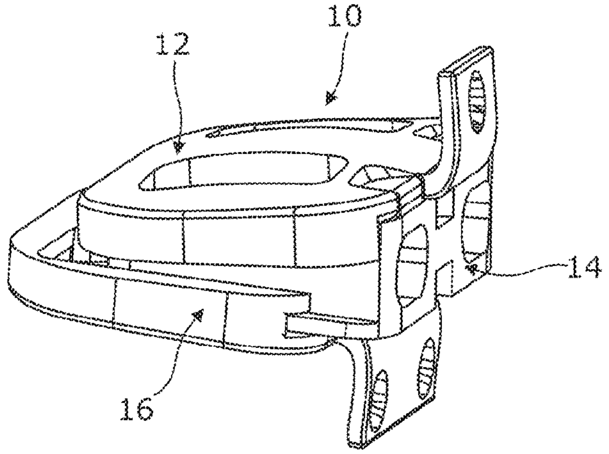
FIG. 1H is a perspective view from above of the first embodiment of anterior lumbar interbody fusion device when assembled and before correction of spondylolisthesis.
Figure 1I:
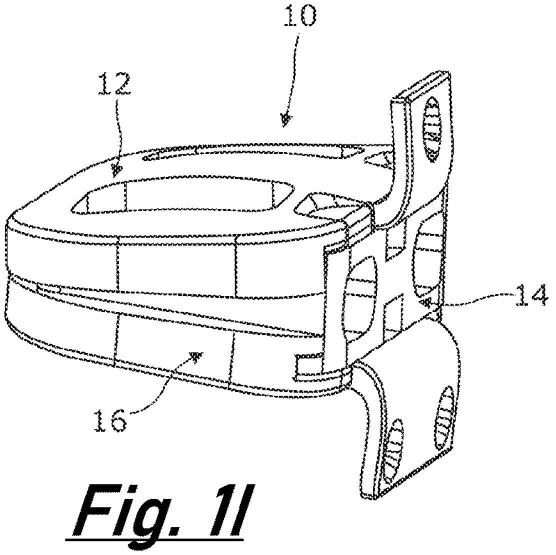
FIG. 1I is a perspective view from above of the first embodiment of anterior lumbar interbody fusion device when assembled and after correction of spondylolisthesis.

As overlap of the core and inferior components 14, 16 increases beyond fifty percent, the protrusion 78 on each of the first and second inferior cantilever spring structures 76 is received under spring bias in successive recesses in a respective one of the first and second sets of plural recesses 54. The surgeon can therefore reduce the extent of spondylolisthesis stage by stage until the spondylolisthesis is properly reduced with operation of the first locking mechanism at each stage of reduction presenting resistance to spondylolisthesis increasing movement. FIG. 1H shows the anterior lumbar interbody fusion device 10 before correction of a Grade 2 spondylolisthesis. FIG. 1I shows the anterior lumbar interbody fusion device 10 after correction of the spondylolisthesis.

The first embodiment of anterior lumbar interbody fusion device 10 has dimensions appropriate for use as such. The superior component has a range of length by width from 20 mm by 20 mm to 50 mm by 50 mm. The superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

As shown in FIG. 1E, the plural recesses 154 are defined in the half of the core component 14 closer to the trailing end of the core component. The leading end of the core component is the end first received between the superior and inferior components. The trailing end of the core component is the end last received between the superior and inferior components. In another unillustrated form of the first embodiment, the plural recesses 154 are defined in the half of the core component 14 closer to the leading end of the core component. In this form of the first embodiment, each of the two inferior cantilever spring structures 76 is attached at its proximal end to near the anterior end (which constitutes the trailing end) of the inferior component 16 and extends to near the posterior end (which constitutes the leading end) of the inferior component. In a further unillustrated form of the first embodiment, the plural recesses 154 are defined by the inferior component 16 and the two inferior cantilever spring structures 76 are comprised in the core component 14.

Figure 2A:
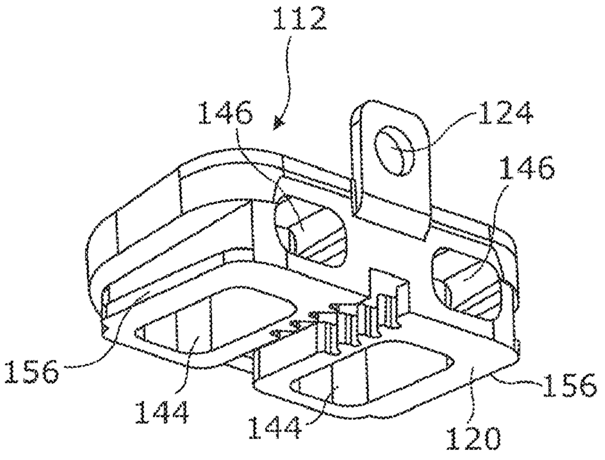
FIG. 2A is a perspective view from a corner and below of a superior component of a second embodiment of anterior lumbar interbody fusion device.
Figure 2B:
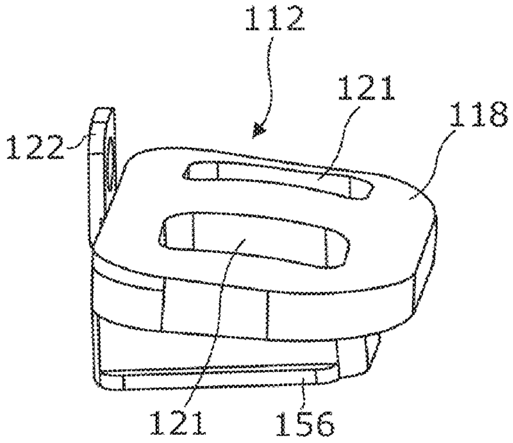
FIG. 2B is a perspective view from above of the superior component of FIG. 2A.
Figure 2C:
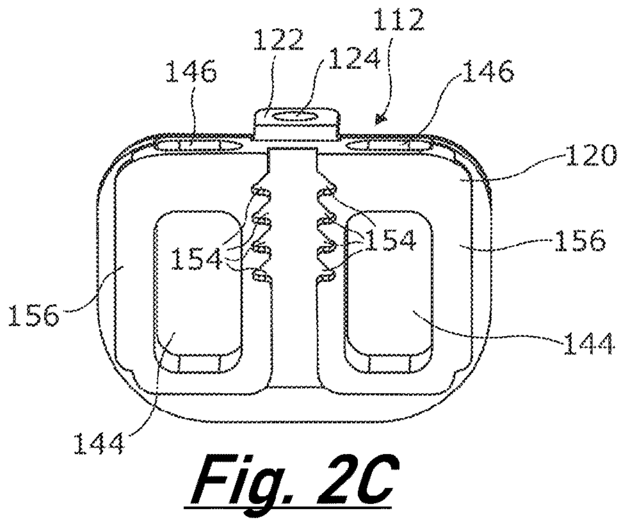
FIG. 2C is a view from below of the superior component of FIG. 2A.
Figure 2D:
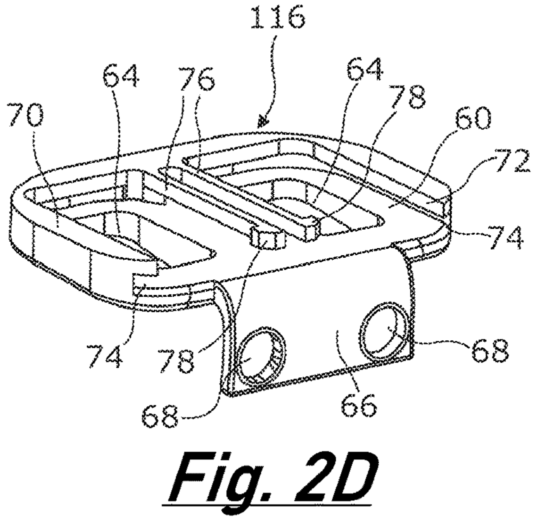
FIG. 2D is a perspective view from above of an inferior component of the second embodiment of anterior lumbar interbody fusion device.
Figure 2E:
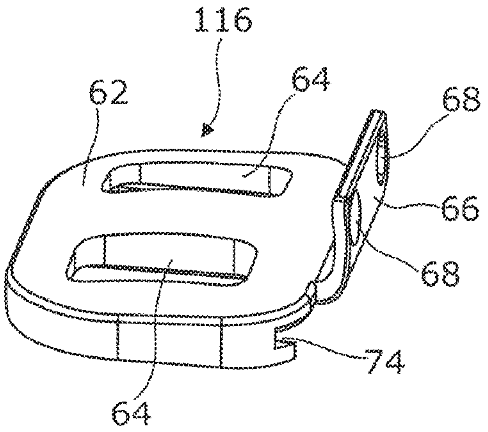
FIG. 2E is a perspective view from below of the inferior component of FIG. 2D.
Figure 2F:
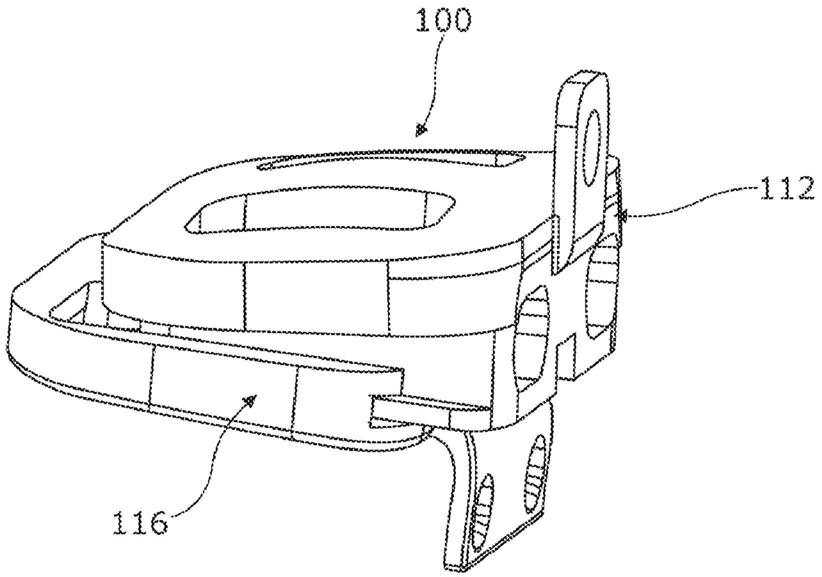
FIG. 2F is a perspective view from above of the second embodiment of anterior lumbar interbody fusion device when assembled and before correction of spondylolisthesis.

A second embodiment of anterior lumbar interbody fusion device 100 is shown in FIGS. 2A to 2G. As described above in respect of the first embodiment, the present embodiment of anterior lumbar interbody fusion (ALIF) device is introduced into a patient's intervertebral space between first and second adjacent vertebrae from the anterior side of the patient. The second embodiment of anterior lumbar interbody fusion device 100 comprises a superior component 112 (which constitutes a superior endplate) and an inferior component 116 (which constitutes an inferior endplate). Perspective views of the superior component 112 from below and above are shown respectively in FIGS. 2A and 2B. A view of the superior component 112 from below is shown in FIG. 2C. Perspective views of the inferior component 116 from above and below are shown respectively in FIGS. 2D and 2E. FIG. 2F is a perspective view from above of the second embodiment of anterior lumbar interbody fusion device 100 when assembled and installed in an intervertebral space of a patient and before correction of spondylolisthesis. FIG. 2F shows the anterior lumbar interbody fusion device 100 before correction of a Grade 2 spondylolisthesis.

Figure 2G:
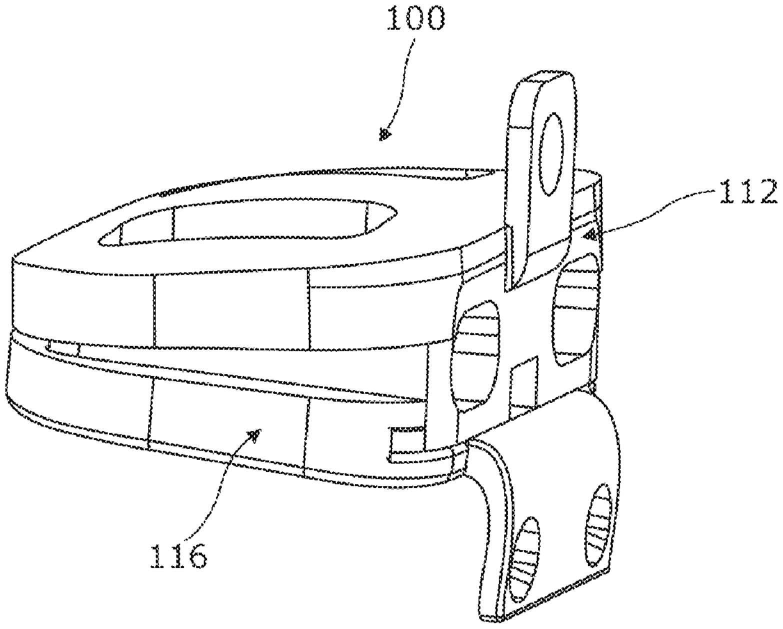
FIG. 2G is a perspective view from above of the second embodiment of anterior lumbar interbody fusion device when assembled and after correction of spondylolisthesis.

FIG. 2G is a perspective view from above of the second embodiment of anterior lumbar interbody fusion device 100 when assembled and after correction of the spondylolisthesis. As may be appreciated from inspection of FIGS. 2A to 2G, the second embodiment of anterior lumbar interbody fusion device 100 lacks the core component of the first embodiment with the core component of the first embodiment being, in effect, an integral part of the superior component 112.

The inferior component 116 is generally of the form of a plate, albeit a plate having structures thereon and two spaced apart apertures therethrough. The superior component 112 has the form of a frustum of a wedge. The second embodiment of anterior lumbar interbody fusion device 100 is assembled and installed in the intervertebral space first by insertion of the inferior component 116 into the intervertebral space with the inserted inferior component fixed with screws to the lower or second vertebra either at this stage or after the spondylolisthesis has been corrected. Then the superior component 112 is inserted into the intervertebral space. When the superior component 112 is being inserted into the intervertebral space, the superior component is aligned with the inferior component 116 such that the superior component slidably inter-engages with the inferior component. The superior component 112 is then moved in the posterior direction relative to the inferior component 116 such that the extent of overlap of the superior and inferior components 112, 116 increases until the superior component 112 is aligned with the upper or first vertebra. The surgeon then fixes the superior component 112 with a screw to the upper vertebra. Alternatively screw fixing is after the spondylolisthesis has been corrected. At this stage in the procedure, the anterior lumbar interbody fusion device 100 has the disposition shown in FIG. 2F which reflects the extent of spondylolisthesis before correction. The surgeon then manipulates the patient to correct the spondylolisthesis with this involving further movement of the superior component 112 in the posterior direction relative to the inferior component 116 to increase the extent of overlap of the superior and inferior components until the spondylolisthesis is corrected. At this stage in the procedure, the anterior lumbar interbody fusion device 100 has the disposition shown in FIG. 2G. As described further below, the anterior lumbar interbody fusion device 100 is configured to resist spondylolisthesis increasing movement of the superior component 112 in the anterior direction.

Turning now to FIGS. 2A to 2C, the superior component 112 is integrally formed from a metal or plastics material and has a superior component top side 118 and a superior component bottom side 120. The superior component 112 is of a size such that it can be received in the intervertebral space whereby the superior component top side 118 abuts against the upper vertebra. The superior component 112 defines two apertures 121 which extend therethrough and are spaced apart from each other in the transverse direction. The two apertures 121 allow for passage of bone graft material from inside the anterior lumbar interbody fusion device 100. The superior component 112 has an integrally formed superior lug 122 which extends from an anterior end of the superior component and substantially orthogonally to the superior component top side 118 such that the superior lug extends above the superior component top side. The superior lug 122 defines a superior lug aperture 124 extending therethrough. As described above, the surgeon aligns the superior component 112 with the upper vertebra and fixes the superior component 112 with a screw to the upper vertebra either during the procedure or after the spondylolisthesis has been corrected. Considering this latter part of the surgical procedure further, the superior component 112 is aligned with the upper vertebra by moving the superior component 112 in the posterior direction into the intervertebral space until the superior lug 122 abuts against the anterior aspect of the upper vertebra. The surgeon then drives the screw through the superior lug aperture 124 and into the upper vertebra to fix the superior component 112 to the upper vertebra.

As may be appreciated from FIG. 2B, the superior component top side 118 and the superior component bottom side 120 are inclined to each other and do not meet at an acute angle whereby the superior component 112 has the form of a frustum of a wedge with the thickest part of the wedge at the anterior side of the superior component. Furthermore, the superior component 116 defines two bone graft material receiving spaces 144 which are spaced apart from each other in the transverse direction with each bone graft material receiving space extending up from the superior component bottom side 120 to their respective apertures 121 at the superior component top side 118. Two spaced apart bone graft material receiving apertures 146 are defined in the anterior side of the superior component 112 such that they are spaced apart from each other in the transverse direction. Each bone graft material receiving aperture 146 is in fluid communication with a respective one of the two bone graft material receiving spaces 144 whereby bone graft material can be introduced into the receiving space 144 by way of the bone graft material receiving aperture. When the superior component 112 is installed in the intervertebral space, bone graft material held in the bone graft material receiving spaces 144 passes through the two apertures 121 in the superior component to thereby help provide for fusion with the adjacent vertebra. Likewise, bone graft material held in the bone graft material receiving spaces 144 passes through two apertures in the inferior component 116. The inferior component 116 is described below.

Considering FIGS. 2A and 2B in particular, the superior component 12 defines integrally formed structures at the superior component bottom side 120. The structures on the superior component bottom side 120 comprise a channel which extends between the anterior and posterior ends of the superior component such that it bisects the superior component. First and second sets of plural recesses 154 are defined in each of the opposing walls of the channel (each set of plural recesses constitutes a linear rack of a ratchet). The plural recesses 154 defined in each wall are equally spaced apart in the anterior-posterior direction. Also, the set of plural recesses 154 in one wall are in registration with the set of plural recesses 154 in the other wall such that each recess in one wall is in registration with a recess in the other wall. The plural recesses 154 in each wall are shaped to form a toothed rack which permits movement of a protrusion comprised in the inferior component 116 in the anterior direction only of the posterior and anterior directions. The superior component bottom side 120 further comprise first and second ledges 156. Each ledge 156 projects in the transverse direction from a respective transverse side of the superior component 112 and extends between the anterior and posterior sides of the superior component. Each ledge 156 projects from its transverse side with one side of the ledge being planar with and an extension of the superior component bottom side 120 whereby the ledge projects from an edge between the transverse side and the superior component bottom side 120.

Turning now to FIGS. 2D and 2E, the inferior component 116 of the present embodiment is integrally formed from a metal or plastics material and is of the same form as the inferior component 16 of the first embodiment. Features of the inferior component 116 of the second embodiment are designated with reference numerals in common with features of the inferior component 16 of the first embodiment. The reader's attention in respect of features of the inferior component 116 of the second embodiment is therefore directed to the description of the inferior component 16 of the first embodiment provided above with reference to FIGS. 1F and 1G.

As described above, the surgical procedure involves installing the inferior component 116 in the intervertebral space. The superior component 112 is then brought into inter-engagement with the inferior component 116 installed in the intervertebral space. Alternatively, the superior component 112 is brought into preliminary inter-engagement with the inferior component 116 before they are both installed in the intervertebral space. The superior component 112 is brought into inter-engagement with the inferior component 116 by positioning the posterior side of the superior component in front of and relative to the anterior side of the inferior component 116. The posterior end of the superior component 112 is fitted between the anterior ends of the first and second walls 70, 72 of the inferior component 116 such that each ledge 156 is slidably received in a respective channel 74. As the posterior end of the superior component 112 is fitted in this fashion, the ends of the first and second inferior cantilever spring structures 76 abut against respective curved edges of the channel in the superior component. The superior component 112 is then slid in the posterior direction such that there is a progressive increase in an extent of overlap of the superior and inferior components as the posterior end of the superior component moves towards the posterior end of the inferior component. As the superior component 112 is slid in the posterior direction, the ends of the first and second inferior cantilever spring structures 76 travel along the curving together walls of the channel whereby the ends of the first and second inferior cantilever spring structures are pressed towards each other and thereby develop spring bias.

As the superior component 112 and the inferior component 116 are approaching about fifty percent overlap with each other, the protrusion 78 on each of the first and second inferior cantilever spring structures 76 is received under spring bias in a first recess in a respective one of the first and second sets of plural recesses 154. As described above, the plural recesses 154 in each set are shaped to form a toothed linear rack which in view of the corresponding shape of the protrusion 78 permits movement of the protrusion relative to the toothed linear rack in the anterior direction only of the posterior and anterior directions. The two sets of plural recesses 154 and the first and second inferior cantilever spring structures 76 constitute the first locking mechanism (or ratchet). The surgeon can therefore cease applying force to reduce the extent of spondylolisthesis whereupon operation of the first locking mechanism presents resistance to movement of the core component in the posterior, spondylolisthesis increasing direction.

As overlap of the superior and inferior components 112, 116 increases beyond fifty percent, the protrusion 78 on each of the first and second inferior cantilever spring structures 76 is received under spring bias in successive recesses in a respective one of the first and second sets of plural recesses 154. The surgeon can therefore reduce the extent of spondylolisthesis stage by stage until the spondylolisthesis is properly reduced with operation of the first locking mechanism at each stage of reduction presenting resistance to spondylolisthesis increasing movement. FIG. 2F shows the second embodiment of anterior lumbar interbody fusion device 100 before correction of a Grade 2 spondylolisthesis. FIG. 2G shows the second embodiment of anterior lumbar interbody fusion device 100 after correction of the spondylolisthesis.

The second embodiment of anterior lumbar interbody fusion device 100 has dimensions appropriate for use as such. The superior component has a range of length by width from 20 mm by 20 mm to 50 mm by 50 mm. The superior component has a range of height at the posterior end from 4 mm to 14 mm. The inferior component has a range of length by width from 20 mm by 20 mm to 50 mm by 50 mm. The inferior component has a range of height at the posterior end from 1 mm to 4 mm.

Figure 3A:
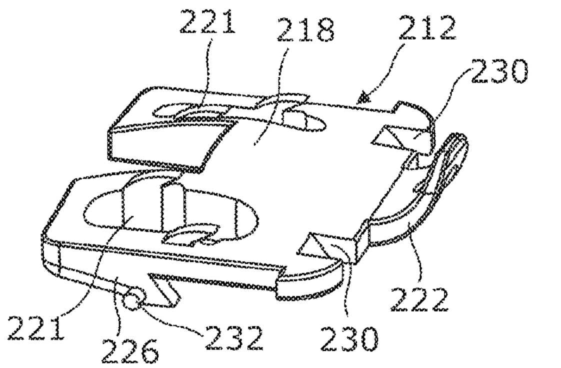
FIG. 3A is a perspective view from above of the superior component of a third embodiment of anterior lumbar interbody fusion device.
Figure 3B:
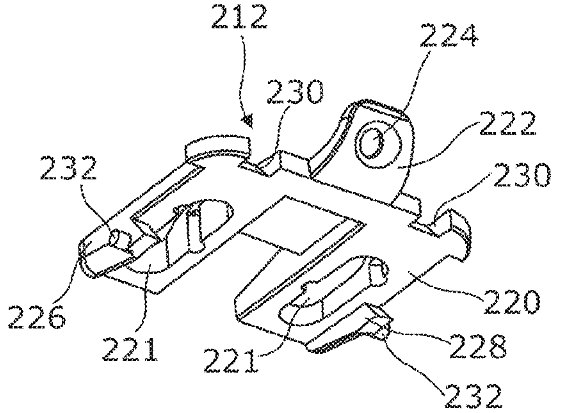
FIG. 3B is a perspective view from below of the superior component of FIG. 3A.
Figure 3C:
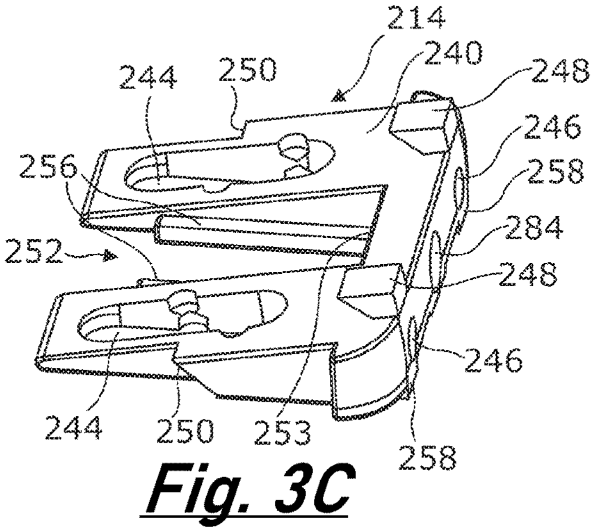
FIG. 3C is a perspective view from above of the core component of the third embodiment of anterior lumbar interbody fusion device.
Figure 3D:
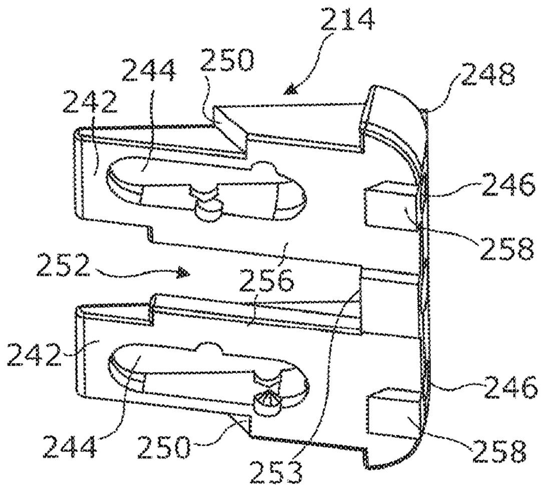
FIG. 3D is a perspective view from below of the core component of FIG. 3C.
Figure 3E:
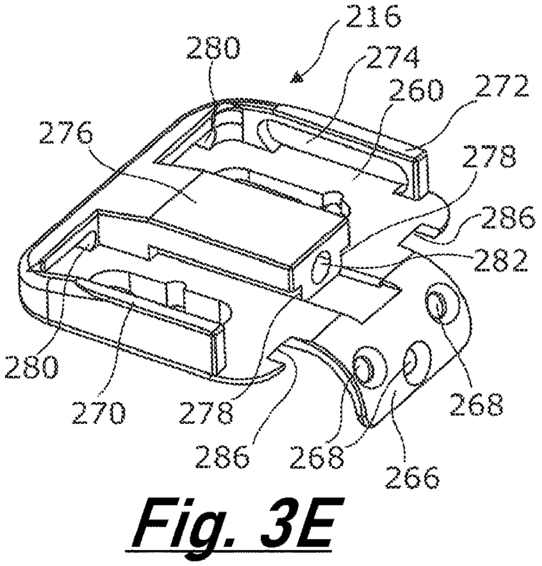
FIG. 3E is a perspective view from above of the inferior component of the third embodiment of anterior lumbar interbody fusion device.
Figure 3F:
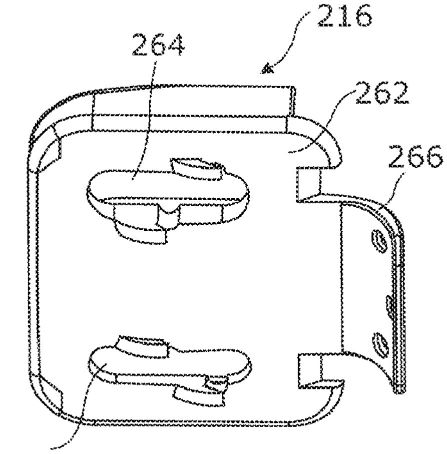
FIG. 3F is a perspective view from below of the inferior component of FIG. 3E.
Figure 3G:
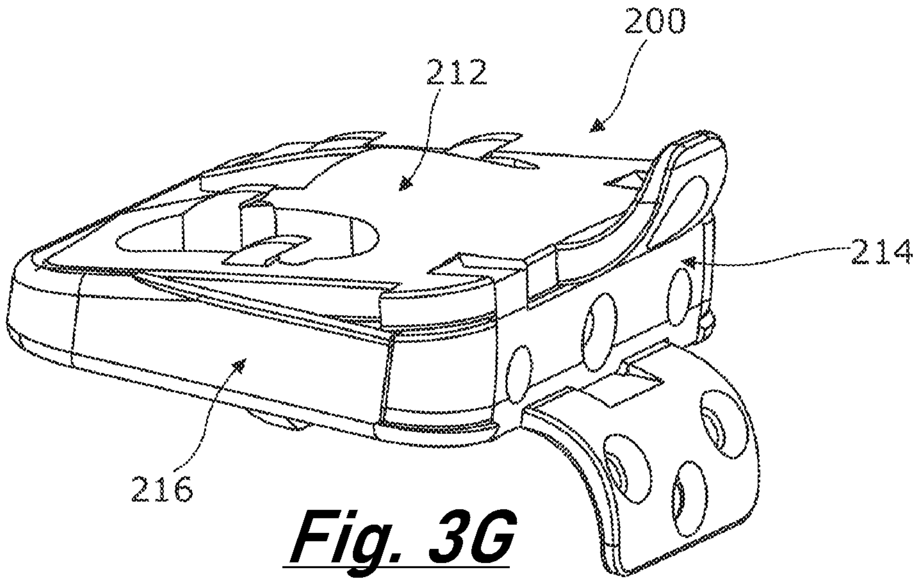
FIG. 3G is a perspective view from above of the third embodiment of anterior lumbar interbody fusion device when assembled and after correction of spondylolisthesis.
Figure 3H:
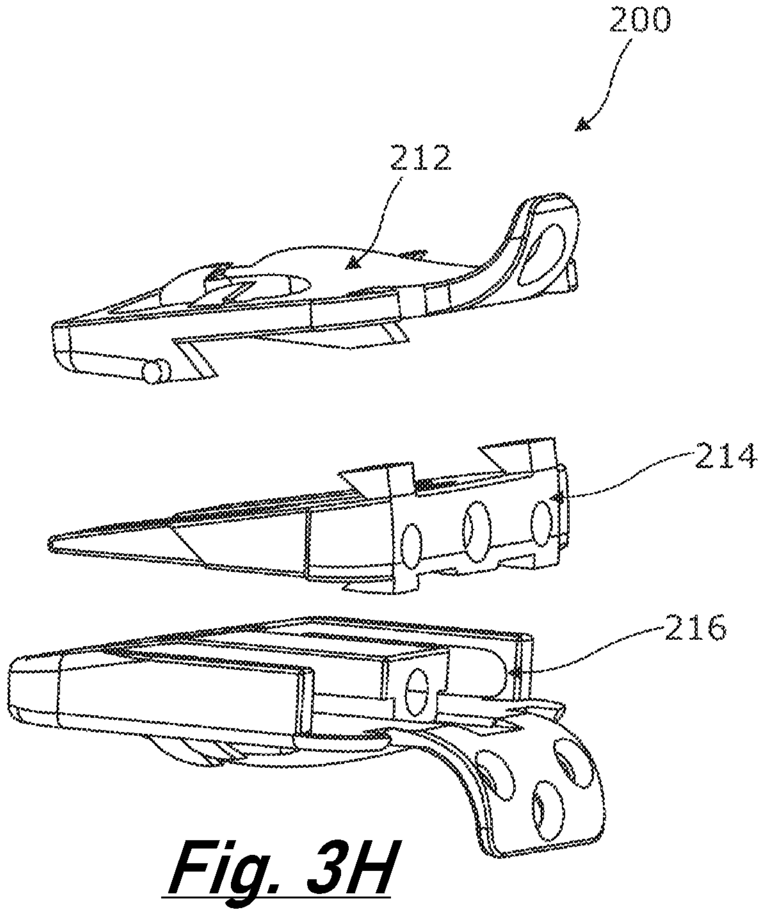
FIG. 3H is an exploded perspective view of the third embodiment of anterior lumbar interbody fusion device.

A third embodiment of anterior lumbar interbody fusion device 200 is shown in FIGS. 3A to 3H. As described above in respect of the first embodiment, the present embodiment of anterior lumbar interbody fusion (ALIF) device is introduced into a patient's intervertebral space between first and second adjacent vertebrae from the anterior side of the patient. The third embodiment of anterior lumbar interbody fusion device 200 comprises a superior component 212 (which constitutes a superior endplate), a core component 214 and an inferior component 216 (which constitutes an inferior endplate). Perspective views of the superior component 212 from above and below are shown respectively in FIGS. 3A and 3B. Perspective views of the core component 214 from above and below are shown respectively in FIGS. 3C and 3D. Perspective views of the inferior component 216 from above and below are shown respectively in FIGS. 3E and 3F. FIG. 3G is a perspective view from above of the third embodiment of anterior lumbar interbody fusion device 200 when assembled and installed in an intervertebral space of a patient and after correction of spondylolisthesis. FIG. 3H is an exploded perspective view of the third embodiment of anterior lumbar interbody fusion device 200.

As may be appreciated from inspection of FIGS. 3A to 3H, the third embodiment in common with the first embodiment of anterior lumbar interbody fusion device 200 comprises a core component. Otherwise, the third embodiment is structured differently from the first embodiment, as will now be described.

Each of the superior component 212 and the inferior component 216 is generally of the form of a plate, albeit a plate having structures thereon and two spaced apart apertures therethrough. The core component 214 has the form of a wedge. The anterior lumbar interbody fusion device 200 is assembled and installed in the intervertebral space first by bringing the superior component 212 and the inferior component 216 into inter-engagement with each other before they are inserted into the intervertebral space. Upon insertion or after correction of the spondylolisthesis, the inferior component 216 is fixed with three screws to the lower or second vertebra. The core component 214 is then inserted between the superior and inferior components 212, 216. When the core component 214 and the superior component 212 are fully inter-engaged, they move together in the intervertebral space relative to the inferior component 216 with the core component slidably inter-engaging with the inferior component. Movement of the superior and core components 212, 214 together in the posterior direction relative to the inferior component 16 increases the extent of overlap of the superior and inferior components 212, 216 until the superior component 212 is aligned with the upper or first vertebra. The surgeon then fixes the superior component 212 with a screw to the upper vertebra. Alternatively, screw fixing is done after correction of the spondylolisthesis. The surgeon then manipulates the patient to correct the spondylolisthesis with this involving further movement of the superior and core components 212, 214 together in the posterior direction relative to the inferior component 216 by way of the screw threaded locking mechanism described below to increase the extent of overlap of the superior and inferior components until the spondylolisthesis is corrected. At this stage in the procedure, the third embodiment of anterior lumbar interbody fusion device 200 has the disposition shown in FIG. 3G. As will become clear from the following description, the third embodiment of anterior lumbar interbody fusion device 200 is configured to resist spondylolisthesis increasing movement of the superior and core components 212, 214 together in the anterior direction.

Turning now to FIGS. 3A and 3B, the superior component 212 is integrally formed from a metal or plastics material and has a superior component top side 218 and a superior component bottom side 220. The superior component 212 is of a size such that it can be received in the intervertebral space whereby the superior component top side 218 abuts against the upper vertebra. The superior component 212 defines two apertures 221 which extend therethrough and are spaced apart from each other in the transverse direction. The two apertures 221 allow for passage of bone graft material from inside the anterior lumbar interbody fusion device 200. The superior component 212 has an integrally formed superior lug 222 which extends from an anterior end of the superior component and substantially orthogonally to the superior component top side 218 such that the superior lug extends above the superior component top side. The superior lug 222 defines a superior lug aperture 224 extending therethrough. As described above, the surgeon aligns the superior component 212 with the upper vertebra and fixes the superior component 212 with a screw to the upper vertebra either during the procedure or after correction of the spondylolisthesis. Considering this latter part of the surgical procedure further, the superior component 212 is aligned with the upper vertebra by moving the superior component 212 in the posterior direction in the intervertebral space until the superior lug 222 abuts against the anterior aspect of the upper vertebra. The surgeon drives the screw through the superior lug aperture 224 and into the upper vertebra to fix the superior component 212 to the upper vertebra.

Considering FIG. 3B in particular, the superior component 212 defines integrally formed structures at the superior component bottom side 220. The structures comprise first and second straight walls 226, 228 which each extend up from the superior component bottom side 220 and away from the superior component top side 218. Each of the first and second walls 226, 228 is towards a respective transverse side of the superior component 212 such that the first and second walls are parallel and face each other. The first and second walls 226, 228 run in the anterior-posterior direction from the posterior end of the superior component 212 halfway towards the anterior end of the superior component. An anterior facing end of each of the first and second walls 226, 228 slopes from the superior component bottom side 220 in a direction towards the posterior end of the core component. As described further below, the first and second walls provide for slidable engagement with the core component 214 and guide movement of the core component relative to the superior component 212 before providing for inter-engagement with the superior component.

The structures in the superior component 212 comprise first and second anterior recesses 230 and first and second cylindrical protrusions 232. The first and second anterior recesses 230 are defined in the anterior edge of the superior component 212 and such that they are spaced apart from each other in the transverse direction. As can be seen from FIG. 3A, the base of each of the first and second anterior recesses 230 is inclined to a plane in which the anterior-posterior direction and the transverse direction lie whereby the base of the recess slopes upwards away from the anterior side. As described further below, a sloped surface of a corresponding protrusion on the core component 214 rides over the sloped base of each anterior recess 230 to draw the core component and superior component together and into inter-engagement. Each of the first and second cylindrical protrusions 232 extends from the outside of a respective one of the first and second walls 226, 228 whereby the first and second cylindrical protrusions 232 lie on the same axis and extend in opposite directions and in the transverse direction. As described further below, the first and second cylindrical protrusions 232 inter-engage with the inferior component 216 and provide for relative movement of the superior component 212 and inferior component 216 in the anterior-posterior direction and for limited relative movement of the superior and inferior components in the direction of separation of the superior and inferior components.

Turning now to FIGS. 3C and 3D, the core component 214 is integrally formed from a metal or plastics material and has an upper side 240 and a lower side 242. As can be seen from FIG. 3H, the upper side 240 and the lower side 242 are inclined to each other and meet at a rounded acute angle whereby the thickest part of the wedge is at the anterior side of the core component. The core component defines two bone graft material receiving spaces 244 which are spaced apart from each other in the transverse direction with each bone graft material receiving space extending from the upper side 240 to the lower side 242. Two spaced apart bone graft material receiving apertures 246 are defined in the anterior side of the core component 214 such that they are spaced apart from each other in the transverse direction. Each bone graft material receiving aperture 246 is in fluid communication with a respective one of the two bone graft material receiving spaces 244 whereby bone graft material can be introduced into the receiving space 244 by way of the bone graft material receiving aperture. When the superior component 212 and the core component 214 are installed in the intervertebral space, bone graft material held in the bone graft material receiving spaces 244 passes through the two apertures 221 in the superior component to thereby help provide for fusion with the adjacent vertebra. Likewise, bone graft material held in the bone graft material receiving spaces 244 passes through two apertures in the inferior component 216, which is described below.

The core component 214 defines integrally formed structures on each of the upper side 240 and the lower side 242. The structures on the upper side 240 of the core component 214 comprise first and second anterior protrusions 248. The first and second anterior protrusions 248 extend up from the upper surface and at the anterior edge of the core component 214 but within the anterior boundary and such that they are spaced apart from each other in the transverse direction. As can be seen from FIGS. 3C and 3D, the posterior facing side of each of the first and second anterior protrusions 248 is inclined to a plane in which the anterior-posterior direction and the transverse direction lie whereby the posterior facing side slopes up and away from the anterior side. The core component 214 also defines first and second shoulders 250 each at a respective transverse side of the core component. The first and second shoulders 250 are halfway along the core component between the anterior and posterior ends. The first and second shoulders 250 are aligned with each other. Each of the first and second shoulders 250 faces towards the posterior end of the core component and slopes upwards from the lower side 242 towards the posterior end.

The core component 214 is brought into inter-engagement with the superior component 212 by first fitting the posterior end of the core component between the ends of the first and second straight walls 226, 228 halfway along the superior component. The width of the core component 214 in the transverse direction and the spacing apart of the first and second straight walls 226, 228 is such that the core component is a snug fit between the first and second straight walls whilst allowing for sliding relative movement of the core and superior components. The core component 214 is then slid in the posterior direction such that there is a progressive increase in an extent of overlap of the core and superior components as the posterior end of the core component moves towards the posterior end of the superior component.

As the posterior end of the core component 214 approaches the posterior end of the superior component 212, the first and second anterior protrusions 248 are received in their respective first and second anterior recesses 230. Further movement of the posterior end of the core component towards the posterior end of the superior component causes the sloped posterior facing side of each of the first and second anterior protrusions 248 to ride up the sloped base of each of the first and second anterior recesses 230 whereby the anterior end of the core component and the anterior end of the superior component are drawn together. Furthermore, and as the posterior end of the core component 214 approaches the posterior end of the superior component 212, each of the first and second shoulders 250 abuts against the sloping anterior facing end of a respective one of the first and second walls 226, 228. Further movement of the posterior end of the core component towards the posterior end of the superior component causes the sloped first and second shoulders 250 to ride up the sloped anterior facing ends of the first and second walls 226, 228 whereby the core component and the superior component are drawn together. Thereafter the core component bears against the superior component by virtue of the first and second shoulders 250 whereby core component and superior component move together in the posterior direction.

The core component 214 defines a channel 252 which extends between and is open at the upper side 240 and the lower side 242. Furthermore, the channel 252 extends in the anterior-posterior direction such that it bisects the core component. The channel 252 terminates near the anterior end of the core component at a transversely extending boundary wall 253 and is open at the posterior end of the core component.

Referring now to FIG. 3D in particular, structures on the lower side 242 of the core component 214 comprise first and second ledges 256. Each ledge 256 projects in the transverse direction from a respective wall of the channel 252. Furthermore, each ledge 256 extends along its respective wall from the boundary wall 253 to about three quarters the distance from the boundary wall to the posterior end of the core component. Each ledge 256 is an extension of and planar with the lower side. The two ledges 256 therefore extend towards and are in registration with each other. The structures on the lower side 242 of the core component 214 also comprise third and fourth anterior protrusions 258. The third and fourth anterior protrusions 258 extend up from the lower surface and at the anterior edge of the core component 214 but within the anterior boundary and such that they are spaced apart from each other in the transverse direction. As can be seen from FIG. 3D, the posterior facing side of each of the third and fourth anterior protrusions 258 is inclined to a plane in which the anterior-posterior direction and the transverse direction lie whereby the posterior facing side slopes up and away from the anterior side.

Turning now to FIGS. 3E and 3F, the inferior component 216 is integrally formed from a metal or plastics material and has an inferior component top side 260 and an inferior component bottom side 262. The inferior component 216 is of a size such that it can be received in the intervertebral space whereby the inferior component bottom side 262 abuts against the lower vertebra. The inferior component 216 defines two apertures 264 which extend therethrough and are spaced apart from each other in the transverse direction. The two apertures 264 allow for passage of bone graft material from inside the anterior lumbar interbody fusion device 200. The inferior component 216 has an integrally formed inferior lug 266 which extends from an anterior end of the inferior component and substantially orthogonally to the inferior component bottom side 262 such that the inferior lug extends above the inferior component bottom side. The inferior lug 266 defines three inferior lug apertures 268 extending therethrough. The three inferior lug apertures 268 are spaced apart in the transverse direction. As described above, the surgeon aligns the inferior component 216 with the lower vertebra and fixes the inferior component 216 to the lower vertebra with screws either during the procedure or after correction of the spondylolisthesis. Considering this part of the surgical procedure further, the inferior component 216 is aligned with the lower vertebra by moving the inferior component 216 in the intervertebral space in the posterior direction until the inferior lug 266 abuts against the anterior aspect of the lower vertebra. The surgeon drives a screw through each of the three inferior lug apertures 268 and into the lower vertebra to fix the inferior component 216 to the lower vertebra.

Considering FIG. 3E in particular, the inferior component 216 defines integrally formed structures at the inferior component top side 260. The structures comprise first and second walls 270, 272 which each extend up from the inferior component top side 260 and away from the inferior component bottom side 262. Each of the first and second walls 270, 272 is at a respective transverse side of the inferior component 216 such that the first and second walls are parallel and face each other. The first and second walls 270, 272 run in the anterior-posterior direction. An elongate recess 274 is defined in the inside surface of each of the first and second walls 270, 272. Each elongate recess 274 extends a substantial distance between the anterior and posterior ends of the inferior component 216. The two elongate recesses 274 are in registration with and oppose each other. The inferior component 216 comprises an integrally formed island 276 of rectangular outline when viewed from the inferior component top side 260. The island 276 extends between the anterior and posterior ends of the inferior component and such that it is centrally disposed on a line which extends in the anterior-posterior direction and bisects the inferior component. The island 276 defines first and second elongate channels 278 in oppositely directed side walls of the island and such that the inferior component top side 260 constitutes the lower side of each channel. The channels 278 extend from the anterior end of the island 276 to near the posterior end of the island. The channels 278 are in registration with and face away from each other.

The inferior component 216 also defines first and second posterior recesses 280 which are defined at the proximal end of a posterior wall extending up from the inferior component top side 260. The first and second posterior recesses 280 are on opposite sides of the island 276 whereby the first and second posterior recesses are spaced apart from each other in the transverse direction. The island 276 defines a threaded bore 282 in the anterior end face of the island. The inferior component 216 also defines first and second anterior recesses 286. The first and second anterior recesses 286 are defined in the anterior edge of the inferior component 216 and such that they are spaced apart from each other in the transverse direction. As can be seen from FIG. 3F, the base of each of the first and second anterior recesses 286 is inclined to a plane in which the anterior-posterior direction and the transverse direction lie whereby the base of the recess slopes upwards away from the anterior side.

The surgical procedure involves either bringing the superior, core and inferior components 212, 214, 216 into inter-engagement with one another before they are installed in the intervertebral space or installing the superior and inferior components 212, 216 in the intervertebral space and inserting the core component 214 between the superior and inferior components. Irrespective of the approach followed, the superior and inferior components 212, 216 are attached to each other by fitting each one of the first and second cylindrical protrusions 232 into a respective one of the elongate recesses 274. When the superior and core components 212, 214 have been brought into preliminary inter-engagement, the core component is then brought into inter-engagement with the inferior component 216. The core component 214 is brought into inter-engagement with the inferior component 216 by positioning the posterior side of the core component in front of the anterior side of the inferior component 216. The small extent of movement of the first and second cylindrical protrusions 232 in their respective elongate recesses 274 allows for core components of different heights to be brought into use. The posterior end of the core component 214 is fitted between the anterior ends of the first and second walls 270, 272 of the inferior component 216 and such that each ledge 256 is slidably received in a respective channel 278. The core component 214 is then slid in the posterior direction such that there is a progressive increase in an extent of overlap of the core and inferior components as the posterior end of the core component moves towards the posterior end of the inferior component.

A threaded bolt (not shown) is fed through a bolt aperture 284, which extends through the centre of the anterior end of the core component 214 and is brought into threaded engagement with the threaded bore 282 in the anterior end face of the island 276. The threaded bolt is used to drive the core component 214 relative to the inferior component 216 against resistance presented by the spondylolisthesis to increase an extent of overlap of the core and inferior components and thereby reduce the extent of spondylolisthesis towards what is shown in FIG. 3G. The resistance presented by inter-engagement of the threaded bolt and the threaded bore 282 presents resistance to relative movement which would be liable to decrease extent of overlap of the core and inferior components, whereby the extent of spondylolisthesis can be decreased stage-by-stage by the surgeon as described above. As the posterior end of the core component 214 approaches the posterior end of the inferior component 216, each of the third and fourth anterior protrusions 258 on the core component is received in a respective one of the first and second anterior recesses 286 in the inferior component and such that their sloping surfaces ride over each other to draw and hold together the core and inferior components at their anterior ends. The first and second posterior recesses 280 in the inferior component receive anatomical matter and material sloughed from the anterior lumbar interbody fusion device 200 which might otherwise be liable to become trapped behind the core component 214 to thereby prevent the core component 214 being received fully between the superior and inferior components 212, 216.

The third embodiment of anterior lumbar interbody fusion device 200 has dimensions appropriate for use as such. The superior component has a range of length by width from 20 mm by 20 mm to 50 mm by 50 mm. The superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

Figure 4A:
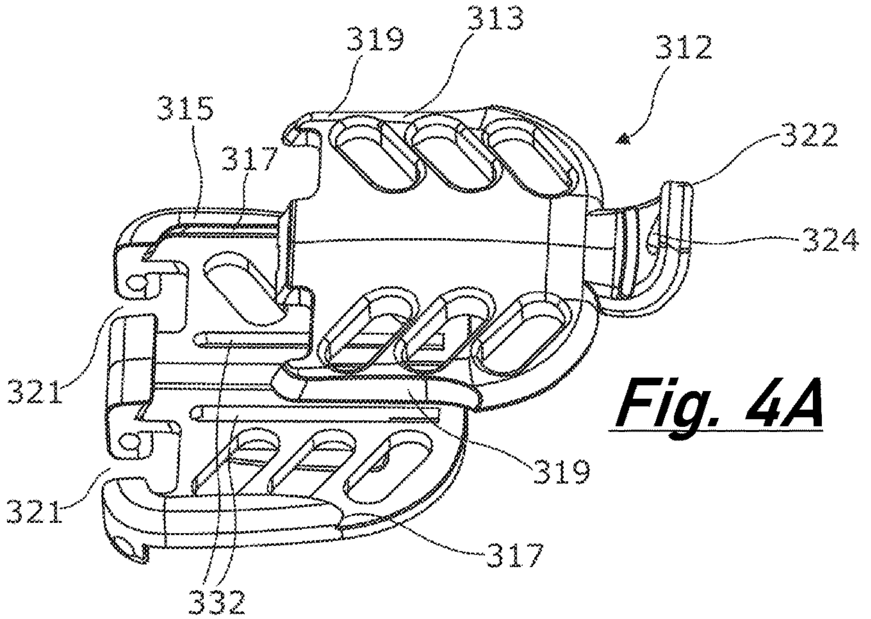
FIG. 4A is a perspective view from above of the superior component of a fourth embodiment of anterior lumbar interbody fusion device.
Figure 4B:
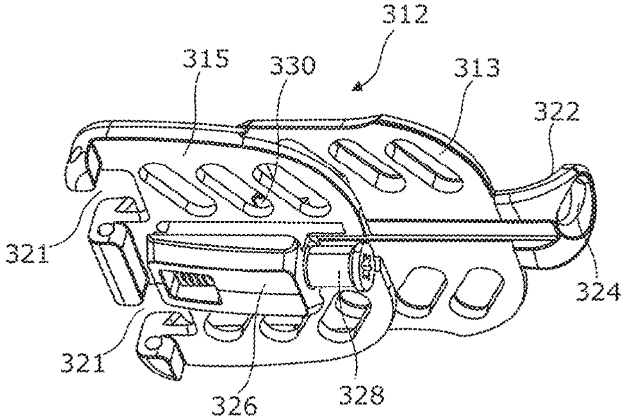
FIG. 4B is a perspective view from below of the superior component of FIG. 4A.
Figure 4C:
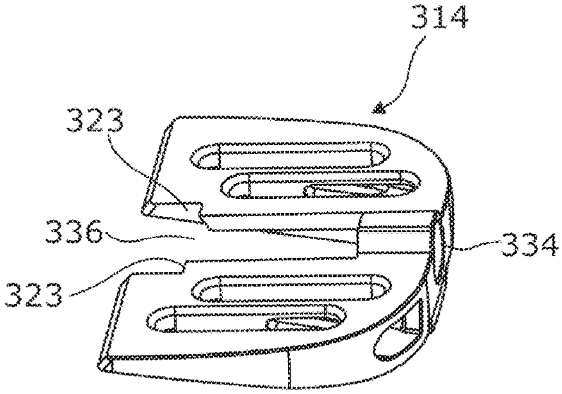
FIG. 4C is a perspective view from above of the core component of the fourth embodiment of anterior lumbar interbody fusion device.
Figure 4D:
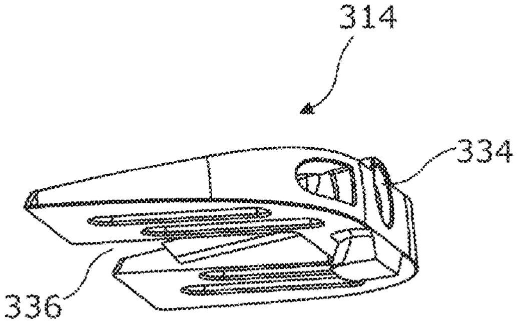
FIG. 4D is a perspective view from below of the core component of FIG. 4C.
Figure 4E:
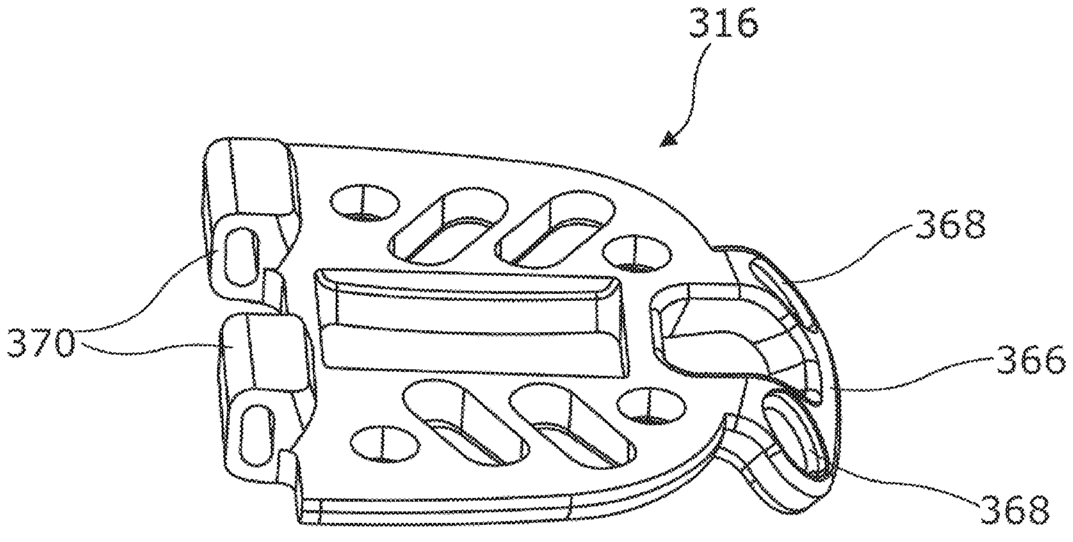
FIG. 4E is a perspective view from above of the inferior component of the fourth embodiment of anterior lumbar interbody fusion device.
Figure 4F:
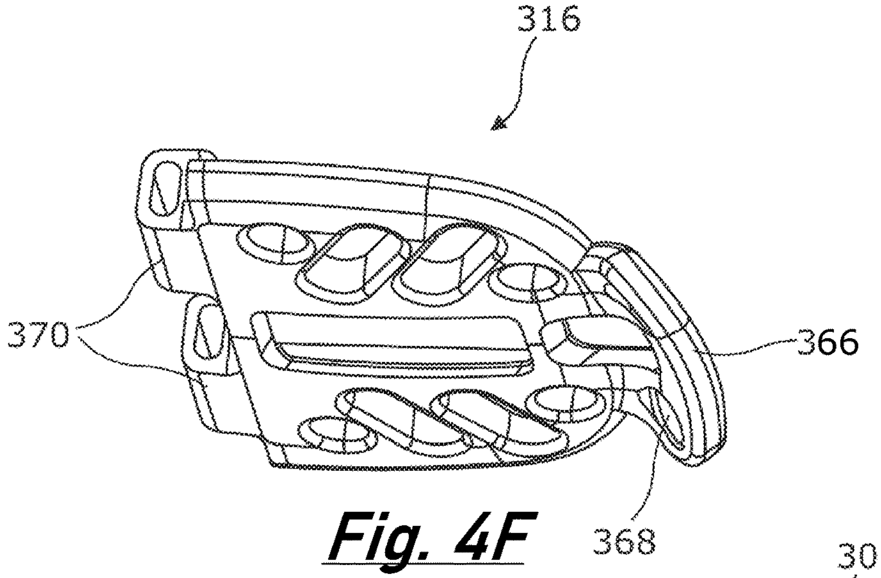
FIG. 4F is a perspective view from below of the inferior component of FIG. 4E.
Figure 4G:
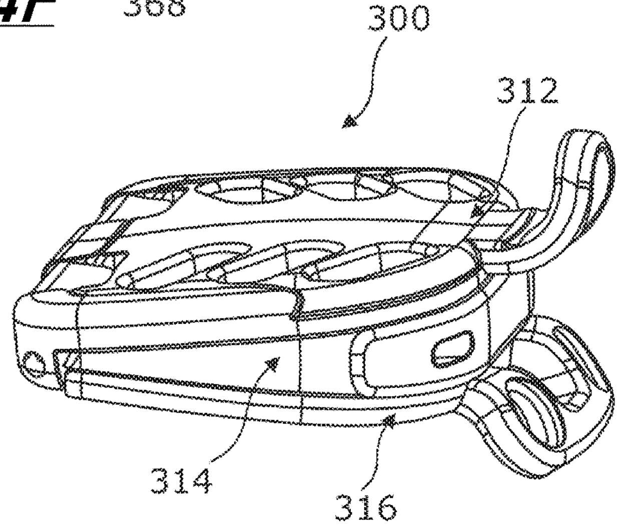
FIG. 4G is a perspective view from above of the fourth embodiment of anterior lumbar interbody fusion device when assembled and after correction of spondylolisthesis.

A fourth embodiment of anterior lumbar interbody fusion device 300 is shown in FIGS. 4A to 4G. As described above in respect of the first embodiment, the present embodiment of anterior lumbar interbody fusion (ALIF) device is introduced into a patient's intervertebral space between first and second adjacent vertebrae from the anterior side of the patient. The third embodiment of anterior lumbar interbody fusion device 300 comprises a superior component 312 (which constitutes a superior endplate), a core component 314 and an inferior component 316 (which constitutes an inferior endplate). Perspective views of the superior component 312 from above and below are shown respectively in FIGS. 4A and 4B. Perspective views of the core component 314 from above and below are shown respectively in FIGS. 4C and 4D. Perspective views of the inferior component 316 from above and below are shown respectively in FIGS. 4E and 4F. FIG. 4G is a perspective view from above of the fourth embodiment of anterior lumbar interbody fusion device 300 when assembled and installed in an intervertebral space of a patient and after correction of spondylolisthesis.

As may be appreciated from inspection of FIGS. 4A to 4G, the fourth embodiment 300 is similar in structure to the third embodiment of anterior lumbar interbody fusion device 200.

Each of the superior component 312 (when assembled) and the inferior component 316 is generally of the form of a plate, albeit a plate having structures thereon and two spaced apart apertures therethrough. The core component 314 has the form of a frustum of a wedge. The anterior lumbar interbody fusion device 300 is assembled and installed in the intervertebral space by insertion of the inter-engaged superior and inferior components 312, 316 into the intervertebral space. The inferior component 316 is fixed with two screws to the lower or second vertebra either during the procedure or after correction of the spondylolisthesis. The core component 314 is then inserted between the already installed superior and inferior components. Then a part of the superior component 312 and the core component 314 are moved relative to the inferior component 316 such that the extent of overlap of the core and inferior components 314, 316 increases until the part of the superior component 312 is aligned with the upper or first vertebra. The surgeon then fixes the part of the superior component 312 with a screw to the upper vertebra. Alternatively, the screw fixing is done after correction of the spondylolisthesis. The surgeon then manipulates the patient to correct the spondylolisthesis with this involving further movement of the core component 314 in the posterior direction relative to the inferior component 316 by way of the screw threaded locking mechanism described below to increase the extent of overlap of the superior and inferior components until the spondylolisthesis is corrected. At this stage in the procedure, the fourth embodiment of anterior lumbar interbody fusion device 300 has the disposition shown in FIG. 4G.

Turning now to FIGS. 4A and 4B, the superior component 312 comprises first 313 and second 315 component parts, which are each integrally formed from a metal or plastics material. The first and second component parts 313, 315 inter-engage with each other such that the first component part moves relative to the second component part in the anterior-posterior direction. The second component part 315 defines two channels 317 each at a respective transverse side whereby the channels are spaced apart from and opposing each other. The first component part 313 defines first and second edges 319 at opposite transverse sides which are each shaped to be slidably received in a respective one of the two channels 317 whereby the first component part is constrained to move in the anterior-posterior direction relative to the second component.

The second component part 315 defines a first hinge structure 321 at its posterior end which interdigitates with a corresponding second hinge structure at the posterior end of the inferior component 316 with the first and second hinge structures connected with a hinge pin (not shown) whereby the superior and inferior components are rotatably coupled to each other. The first and second hinge structures are configured to allow for a small amount of movement in the direction in which the superior and inferior components are spaced apart as well as for rotation. The first component part 313 has an integrally formed superior lug 322 which extends from an anterior end of the superior component and substantially orthogonally to the top side of the superior component such that the superior lug extends above the superior component top side. The superior lug 322 defines a superior lug aperture 324 extending therethrough. In use, the first component part 313 abuts against the upper vertebra. The first component part 313 is fixed to the upper vertebra by way of a screw and the superior lug aperture 324, as described above in respect of previous embodiments.

Referring now to FIG. 4B, the lower surface of the second component part 315 has an island 326 extending therefrom. The island 326 is of rectangular outline when viewed in plan and extends in the anterior-posterior direction. A threaded bolt 328 threadedly engages with a threaded bore defined in the island 326. Two projections 330, which are spaced apart in the transverse direction, project from the lower surface of the first component part 313 towards the second component part 315. The second component part 315 defines two parallel elongate apertures 332 which extend therethrough and in the anterior-posterior direction. The two parallel elongate apertures 332 are spaced apart in the transverse direction by a distance corresponding to the spacing apart of the two projections 330. When the first and second component parts 313 and 315 are slidably inter-engaged, as described above, each of the two projections 330 extends through a respective one of the two elongate apertures 332 and such that the projections 330 travel along the elongate apertures 332 as the first component part 313 moves linearly in relation to the second component part 315. As described further below, the distal ends of the two projections 330 abut against a posterior end of the core component 314 whereby movement of the core component in the posterior direction moves the two projections 330 in the posterior direction. The two projections 330 thus mechanically couple the core component 314 to the first component part 313 whereby the core component and the first component part move together in the posterior direction.

Turning now to FIGS. 4C and 4D, the core component 314 is integrally formed from a metal or plastics material. As can be seen from FIG. 4D, the upper and lower sides of the core component 314 are inclined to each other and do not meet at an acute angle whereby the core component has the form of a frustum of a wedge with the thickest part of the wedge at the anterior side of the core component. The anterior end of the core component 314 defines a core bore 334 extending in the anterior-posterior direction. The core component 314 also defines an elongate aperture 336, which is open at the upper and lower sides and at the posterior end of the core component, and which extends in the elongate anterior-posterior direction to a boundary wall near the anterior end. The core bore 334 extends through the boundary wall. The elongate aperture 336 and the island 326 are shaped and sized such that the island is progressively received in the elongate aperture as the core component moves in the posterior direction relative to the second component part 315. The threaded bolt 328 is received through the core bore 334 and threadedly engages with the threaded bore defined in the island 326. Rotation and resulting linear translation of the threaded bolt 328 causes the head of the threaded bolt to bear against the core component 314 to thereby move the core component in the posterior direction. Opposing sides of the elongate aperture 336 define respective shoulders 323 which face in the posterior direction. Each of the two projections 330 described above bears against a respective one of the shoulders 323 whereby movement of the core component causes corresponding movement of the first component part 313. The threaded bolt 328 is thus used to move the first component part 313 in the posterior direction to reduce the extent of spondylolisthesis.

The inferior component 316 of the fourth embodiment is shown in FIGS. 4E and 4F. The inferior component 316 is integrally formed from a metal or plastics material. The inferior component 316 is of a size such that it can be received in the intervertebral space whereby the bottom side of the inferior component abuts against the lower vertebra. The inferior component 316 has an integrally formed inferior lug 366 which extends from an anterior end of the inferior component and substantially orthogonally to the bottom side of the inferior component such that the inferior lug extends above the bottom side. The inferior lug 366 defines two inferior lug apertures 368 extending therethrough. The two inferior lug apertures 368 are spaced apart in the transverse direction. The inferior component 316 defines a second hinge structure 370 at its posterior end which interdigitates with the corresponding first hinge structure 321 at the posterior end of the second component part 315 with the first and second hinge structures connected with a hinge pin (not shown) whereby the superior and inferior components are rotatably coupled to each other. As described above, the surgeon aligns the inferior component 316 with the lower vertebra and fixes the inferior component 316 to the lower vertebra with screws either during the procedure or after correction of the spondylolisthesis. Considering this part of the surgical procedure further, the inferior component 316 is aligned with the lower vertebra by moving the inferior component 316 in the intervertebral space in the posterior direction until the inferior lug 366 abuts against the anterior aspect of the lower vertebra. The surgeon drives a screw through each of the two inferior lug apertures 368 and into the lower vertebra to fix the inferior component 316 to the lower vertebra.

The fourth embodiment of anterior lumbar interbody fusion device 300 has dimensions appropriate for use as such. The first superior component has a range of length by width from 20 mm by 20 mm to 50 mm by 50 mm. The first superior component has a range of height at the posterior end from 1 mm to 4 mm. The second superior component has a range of length by width from 20 mm by 20 mm to 50 mm by 50 mm. The second superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

Figure 5A:
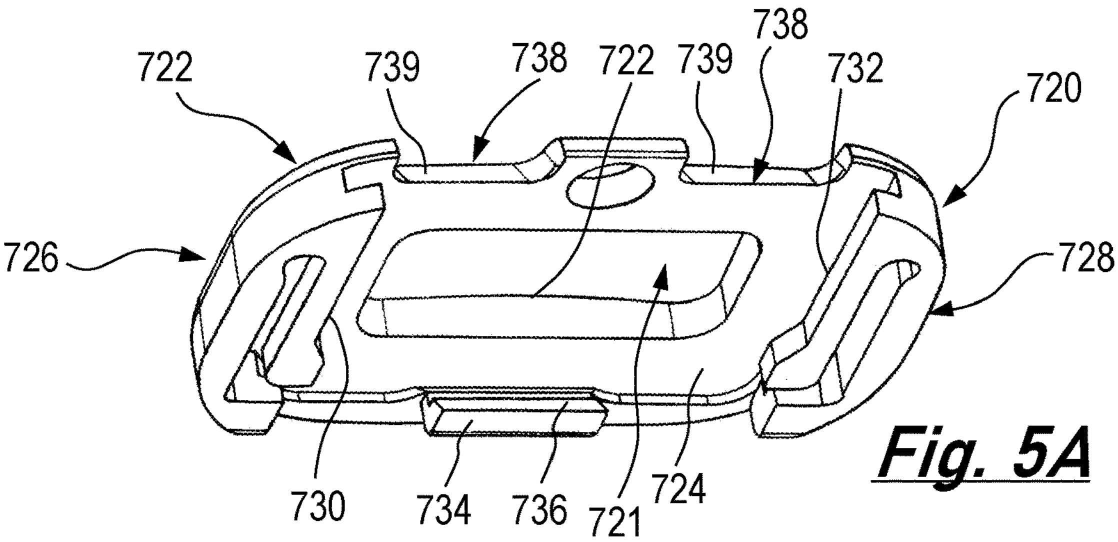
FIG. 5A shows a superior component of a fifth embodiment of the present invention.
Figure 5B:
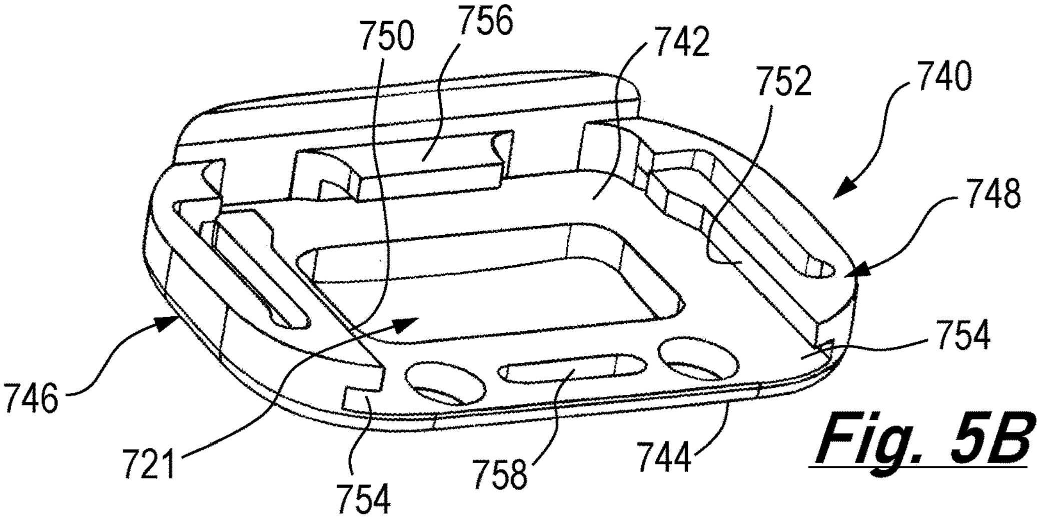
FIG. 5B shows an inferior component of the fifth embodiment of the present invention.
Figure 5C:
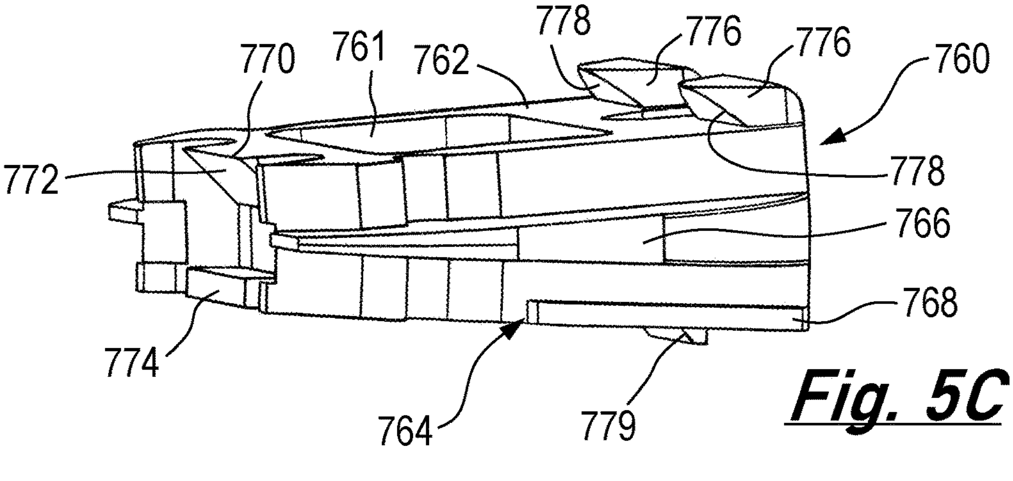
FIG. 5C shows core component of the fifth embodiment of the present invention.
Figure 6A:
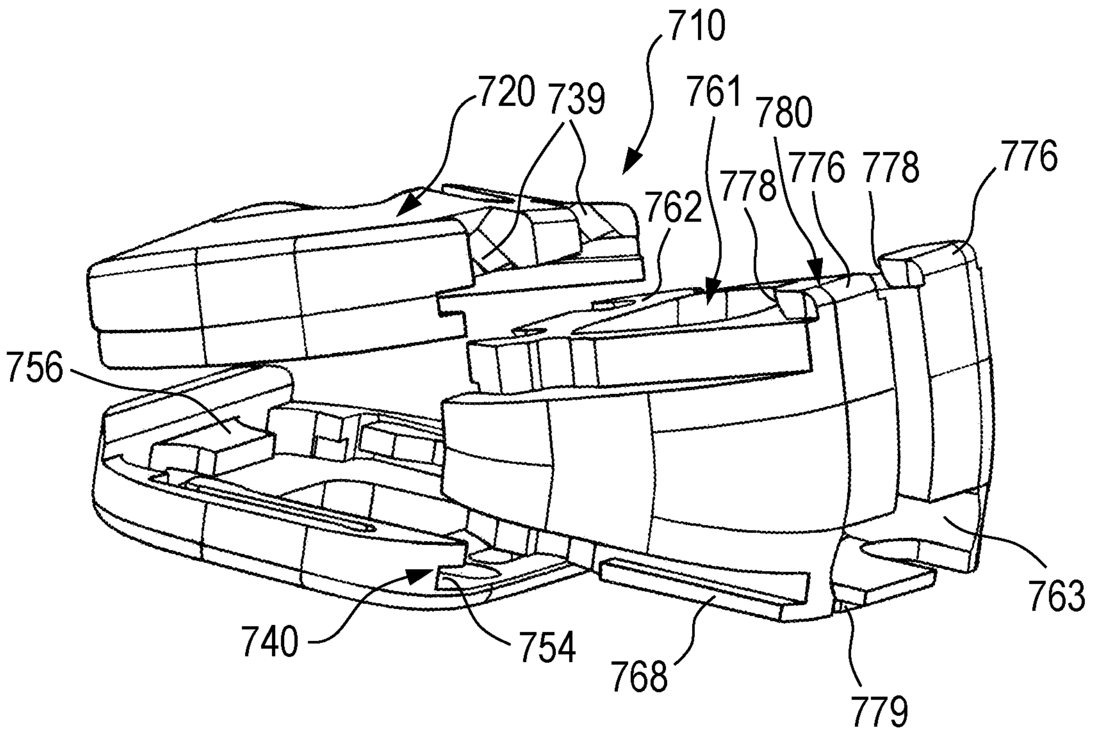
FIG. 6A shows the core component before insertion between the superior and inferior components according to a sixth embodiment.
Figure 6B:
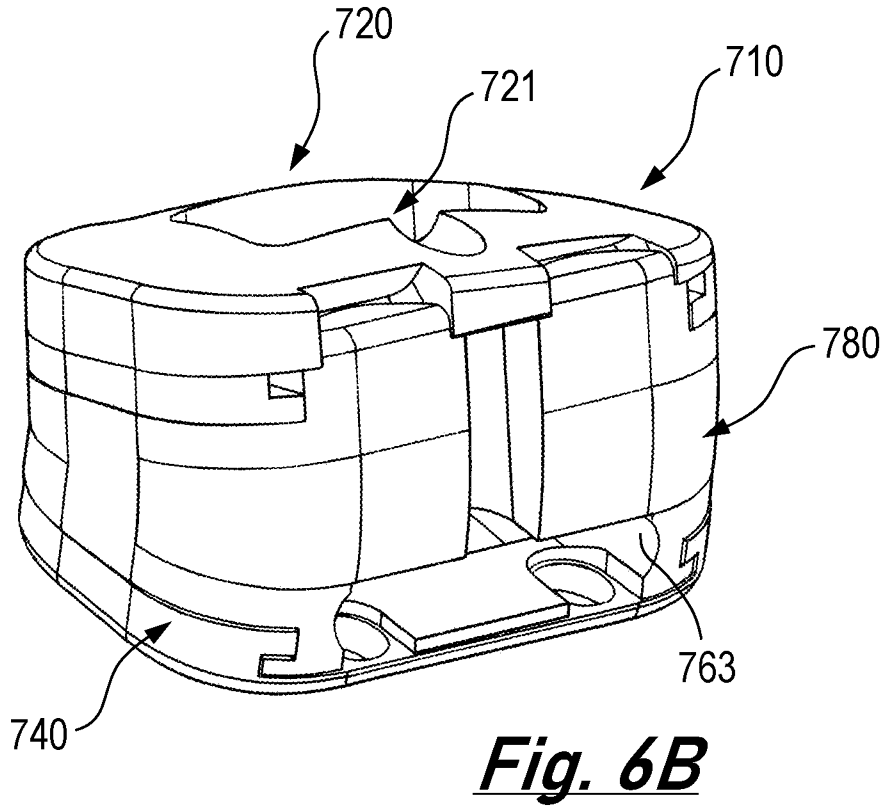
FIG. 6B shows the core component after insertion between the superior and inferior components according to the sixth embodiment.

A superior component, an inferior component and a core component of a fifth embodiment of intervertebral fusion device 710 are shown respectively in FIGS. 5A, 5B and 5C. The intervertebral fusion device 710 is an anterior lumbar interbody fusion (ALIF) device. FIG. 6A shows a core component before insertion between the superior and inferior components of FIGS. 5A and 5B according to a sixth embodiment of intervertebral fusion device with the sixth embodiment differing from the fifth embodiment in respect of the greater height of the core component of the sixth embodiment. FIG. 6B shows the core component of FIG. 6A after insertion between the superior and inferior components.

As mentioned above, the intervertebral fusion device 710 of FIGS. 5A to 6B comprises a superior component 720 (which constitutes a superior endplate), an inferior component 740 (which constitutes an inferior endplate) and a core component 760, 780. Each of the superior component 720 and the inferior component 740 is generally of the form of a plate, albeit a plate having structures thereon and a large aperture therethrough. The core component 760, 780 has the form of a frustum of a wedge. As can be seen from comparison of FIG. 5C with FIGS. 6A and 6B, the core component of FIG. 5C is thinner than the core component of FIGS. 6A and 6B. What is shown in FIGS. 6A and 6B therefore constitutes a sixth embodiment. Use of core components of different thicknesses and/or different extents of tapering wedge and with the same superior component 720 and inferior component 740 provides for different heights and angles of intervertebral fusion device 710. When the intervertebral fusion device 710 is being brought into use, the superior component 720 and the inferior component 740 are placed in the intervertebral space. The core component 760, 780 is positioned relative to the superior component 720 and the inferior component 740 as shown in FIG. 6A. Then the core component 760, 780 is positioned between edges of the superior component 720 and the inferior component 740 with the thin edge, i.e. the leading end, of the core component foremost before the core component is progressively inserted between the superior component and the inferior component until fully received between the superior component and the inferior component. FIG. 6B shows the intervertebral fusion device 710 when the core component 760, 780 is fully received between the superior component 720 and the inferior component 740. When in the disposition shown in FIG. 6B, the superior component top side abuts against a first vertebra defining the intervertebral space in part and the inferior component bottom side abuts against a second vertebra defining the intervertebral space in part.

The superior component 720 will now be described further with reference to FIG. 5A. The superior component 720 has a superior component top side 722, a superior component bottom side 724, a first lateral side 726 and a second lateral side 728. The superior component 720 comprises a first superior component profile 730 and a second superior component profile 732. The first superior component profile 730 is on the first lateral side 726 and the second superior component profile 732 is on the second lateral side 728. The first superior component profile and the first superior core profile, which is described below, abut and the second superior component profile and the second superior core profile, which is described below, abut whereby there is substantially no movement of the core component 760, 780 relative to the superior component 720 in a direction transverse to the direction of insertion of the core component between the superior and inferior components.

The superior component 720 also has a superior component rear formation 734 which extends along a back edge of the superior component in a direction transverse to the direction of insertion of the core component, the back edge being opposite the edge at which the core component is first received upon insertion. The superior component rear formation 734 comprises a protrusion which defines an inclined surface 736. The superior component 720 also has a superior component front formation at an edge at which the core component is first received upon insertion of the core component. The superior component front formation comprises two recesses 738 which are spaced apart in the transverse direction. A surface of each recess 738 facing opposite the direction of insertion of the core component defines an inclined surface 739. The inclined surfaces 739 can be seen more clearly in FIG. 6A.

The inferior component 740 will now be described further with reference to FIG. 5B. The inferior component 740 has an inferior component top side 742, an inferior component bottom side 744, a first lateral side 746 and a second lateral side 748. The inferior component comprises a first inferior component formation 750 and a second inferior component formation 752. The first inferior component formation 750 is towards the first lateral side 746 and the second inferior component formation 752 is towards the second lateral side 748. The first and second inferior component formations 750, 752 oppose each other and are spaced apart in a direction transverse to the direction of insertion of the core component between the inferior and superior components. The core component 760, 780 is received between the first and second inferior component formations 750, 752 during insertion. Each of the first and second inferior component formations 750, 752 defines a groove 754 which extends from the edge of the inferior component 740 that first receives the core component 760, 780 when the core component is being inserted. The opening to the groove 754 faces in the transverse direction.

The inferior component 740 also comprises an inferior component rear formation 756 which extends along a back edge of the inferior component in a direction transverse to the direction of insertion of the core component, the back edge being opposite the edge at which the core component is first received upon insertion. The inferior component rear formation 756 defines an elongate protrusion which is spaced apart from the inferior component top side 742 and which extends in the opposite direction to the direction of insertion of the core component 760, 780. The inferior component 740 defines an elongate aperture 758 near the edge of the inferior component that first receives the core component 760, 780 during insertion. The elongate aperture 758 extends in the transverse direction and is located centrally between the first and second inferior component formations 750, 752.

The core component 760 will now be described further with reference to FIG. 5C. As described above, the core component 760 has the form of a frustum of a wedge. The core component 760 has an upper side 762 and a lower side 764, the core component 760 configured to be inserted between the superior and inferior components 720, 740 such that the upper side 762 faces the superior component bottom side 724 and the lower side 764 faces the inferior component top side 742. The core component 760 has a first lateral side 766 and a second lateral side (not seen in FIG. 5C) which each face in a direction orthogonal to a direction of insertion of the core component and to a direction of separation of the inferior and superior components, with the first and second lateral sides facing in opposite directions. A first inferior core formation 768 is on the first lateral side 766 and a second inferior core formation (not seen in FIG. 5C) is on the second lateral side. The first and second inferior core formations are of the same albeit mirror image form as each other. Each of the first and second inferior core formations 768 defines an elongate protrusion which extends in the transverse direction and from about half way along the core component 760 from the edge of the core component first received between the inferior and superior components to the opposite edge of the core component.

The core component 760 also comprises a superior core rear formation 770 which extends adjacent the upper side 762 and along an edge of the core component which is first received between the inferior and superior components during insertion of the core component. The superior component rear formation 770 comprises a protrusion which defines an inclined surface 772 which faces obliquely away from the core component and down from the upper side 762. The core component 760 further comprises an inferior core rear formation 774 in the form of a protrusion which extends from the lower side 764 and along the edge of the core component which is first received between the inferior and superior components during insertion of the core component.

The core component 760 also comprises a superior core front formation towards an edge opposite the edge first received between the inferior and superior components during insertion of the core component. The superior core front formation comprises two protrusions 776. The two protrusions 776 extend up from the upper side 762 and are spaced apart from each other in the transverse direction. Each of the protrusions 776 defines an inclined surface 778 which faces obliquely down towards the upper side 762 and towards the edge first received between the inferior and superior components during insertion. The core component 760 further comprises in its lower side 764 a living hinge which defines a protrusion 779 thereon. Inherent spring bias of the living hinge urges the protrusion 779 towards the inferior component 740 when the core component 760 is received between the superior and inferior components 720, 740.

As described above, the superior and inferior components 720, 740 are placed in the intervertebral space and the core component 760, 780 is positioned relative to the superior and inferior components as shown in FIG. 6A before the core component is inserted between the superior and inferior components. On initial insertion, the core component is placed generally between the superior and inferior components. During further insertion the core component is moved towards the inferior component until each first inferior core formation 768 is received in its respective groove 754 to thereby present a barrier to separation of the core component from the inferior component in the direction of the superior component. Otherwise and upon the superior component being adjacent the core component, the first and second lateral sides 766 are snugly received between the first and second superior component profiles 730, 732 to guide their relative movement as the core component is progressively inserted whilst the superior component is free to move away from and towards the core component in the direction of separation of the inferior and superior components.

When the core component 760, 780 is approaching full insertion between the inferior and superior components 720, 740 the inferior core rear formation 774 is received under the inferior component rear formation 756 to thereby present a barrier to the edge of the core component lifting from the inferior component. At the same time, the superior core rear formation 770 starts to engage with the superior component rear formation 734 and the two protrusions 776 of the superior core front formation start to engage with the two recesses 738 of the superior component front formation. Considering the superior core rear formation 770 further, the inclined surface 772 of the superior core rear formation 770 slides over the inclined surface 736 of the superior component rear formation 734 to draw the core component and the superior component together at their respective edges. Considering the two protrusions 776 of the superior core front formation further, the inclined surfaces 778 of the protrusions 776 slide over the respective inclined surfaces 739 of the two recesses 738 of the superior component front formation to draw the core component and the superior component together at their respective edges.

When the core component 760, 780 is at full insertion, the protrusion 779 on the living hinge at the lower side 764 of the core component is urged by the inherent spring bias of the living hinge into the elongate aperture 758 in the inferior component. Reception of the protrusion 779 in the elongate aperture 758 presents a barrier to ejection of the core component from between the inferior and superior components.

Figure 7A:
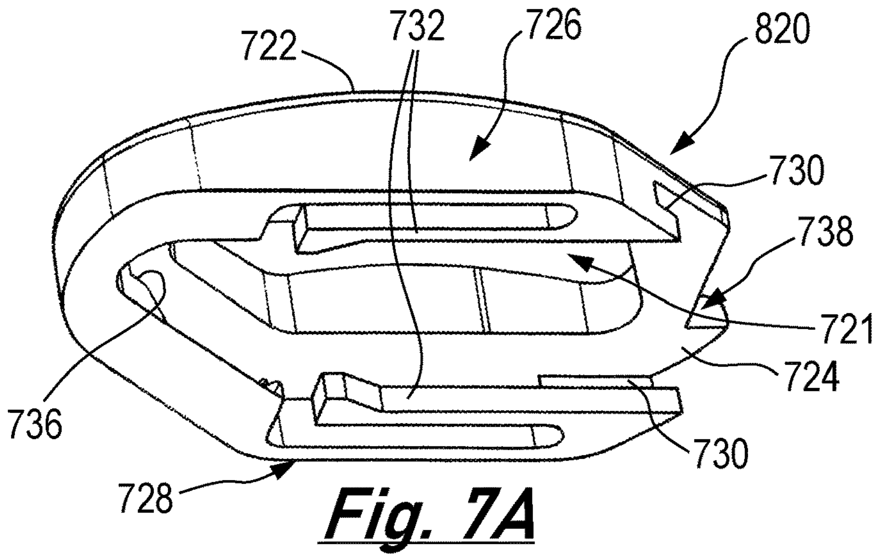
FIG. 7A shows a superior component of a seventh embodiment of the present invention.
Figure 7B:
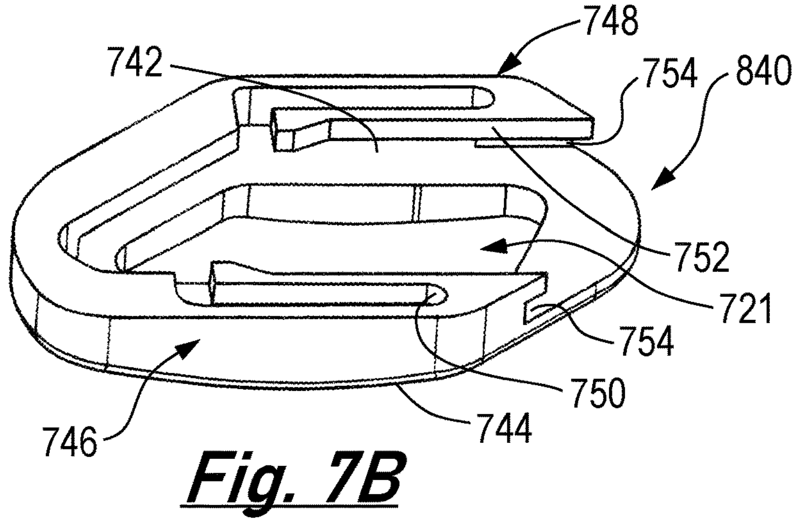
FIG. 7B shows an inferior component of the seventh embodiment of the present invention.
Figure 7C:
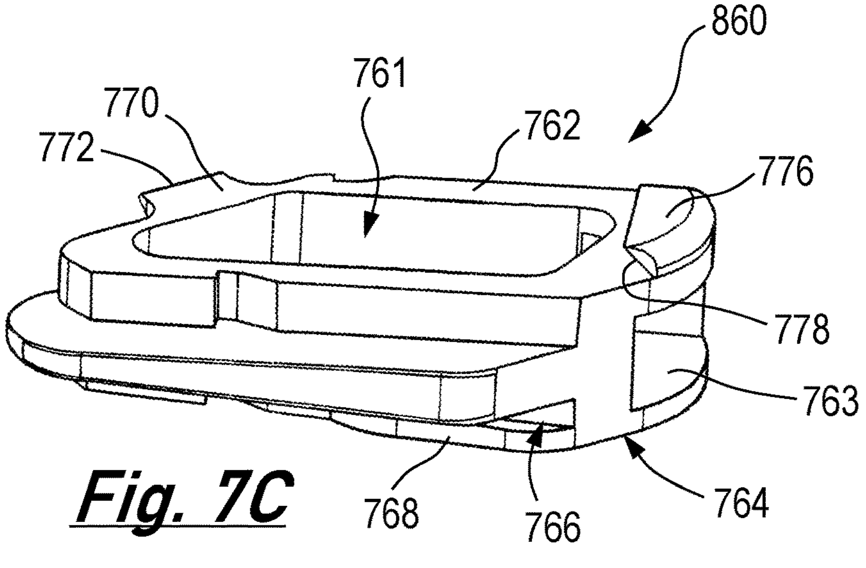
FIG. 7C shows core component of the seventh embodiment of the present invention.
Figure 8A:
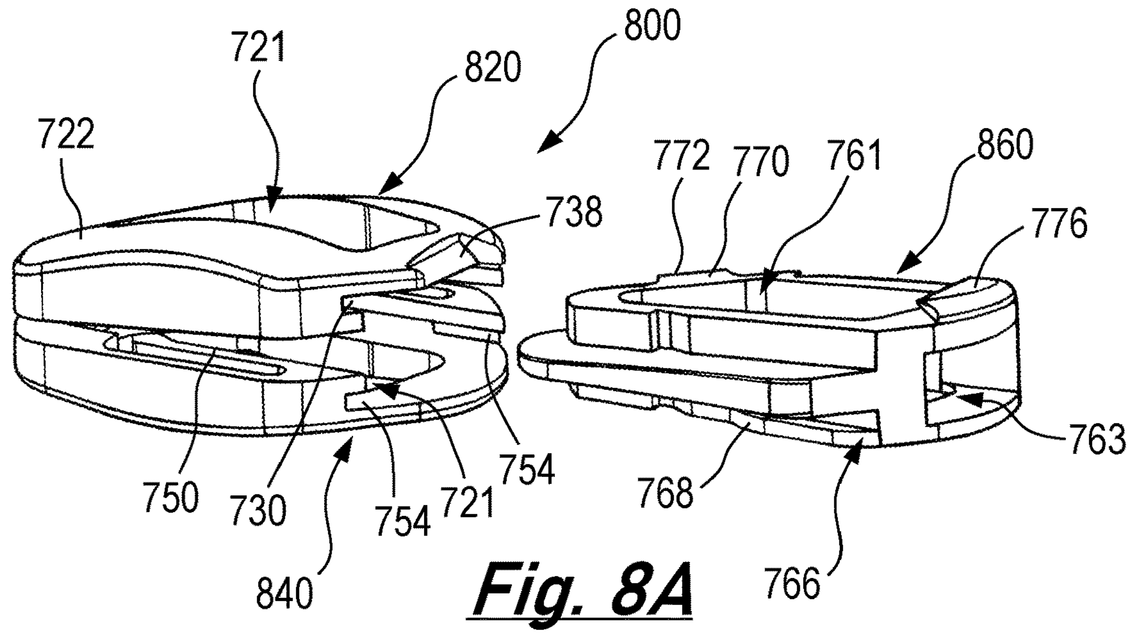
FIG. 8A shows the core component before insertion between the superior and inferior components according to the seventh embodiment.
Figure 8B:
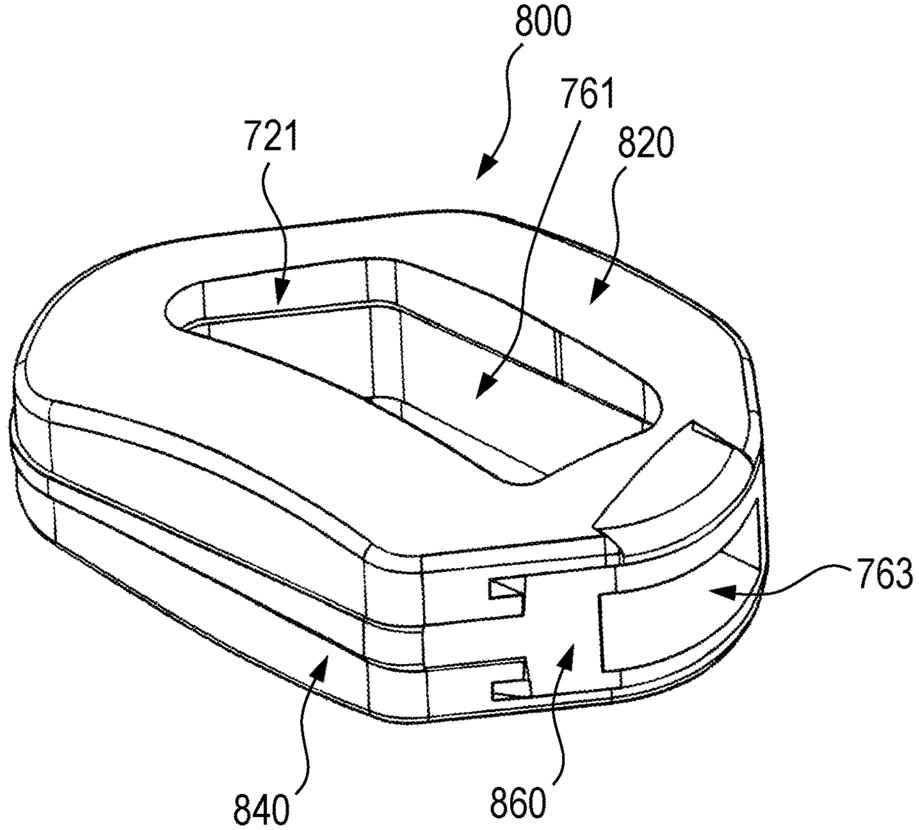
FIG. 8B shows the core component after insertion between the superior and inferior components according to the seventh embodiment.

A seventh embodiment of intervertebral fusion device 800 is shown in FIGS. 7A to 7B. The intervertebral fusion device 800 according to the seventh embodiment is an oblique lateral interbody fusion device. A superior component 820 (which constitutes a superior endplate), an inferior component 840 (which constitutes an inferior endplate), and a core component 860 of the seventh embodiment are shown respectively in FIGS. 7A, 7B and 7C. FIG. 8A shows the core component 860 of the seventh embodiment before insertion between the superior and inferior components 820, 840 of FIGS. 7A and 7B. FIG. 8B shows the core component 860 of the seventh embodiment after insertion between the superior and inferior components 820, 840 of FIGS. 7A and 7B. The superior component 820, the inferior component 840, and the core component 860 of the seventh embodiment are of different shape and dimensions to the fifth and sixth embodiments when viewed in plan whereby the seventh embodiment is configured for insertion into an intervertebral space from an oblique lateral direction. Otherwise, and except as described below, the seventh embodiment is configured in respect of key features in the same fashion as the fifth and sixth embodiments. Such key features are therefore indicated in FIGS. 7A to 8B by the same reference numerals as for the fifth and sixth embodiments and the reader's attention is directed to the preceding description for a description of such key features. In respect of differences, as can be seen from FIG. 7C, the core component 860 has one anterior formation 776 on its upper side instead of the two anterior formations 776 of the fifth and sixth embodiments. Correspondingly, the superior component 820 of the seventh embodiment has one recess 738 at its anterior edge instead of the two recesses of the fifth and sixth embodiments. Furthermore, the seventh embodiment lacks the fifth and sixth embodiments' combination of the protrusion 779 on the living hinge in the core component and the elongate aperture 758 in the inferior component.

Figure 9:
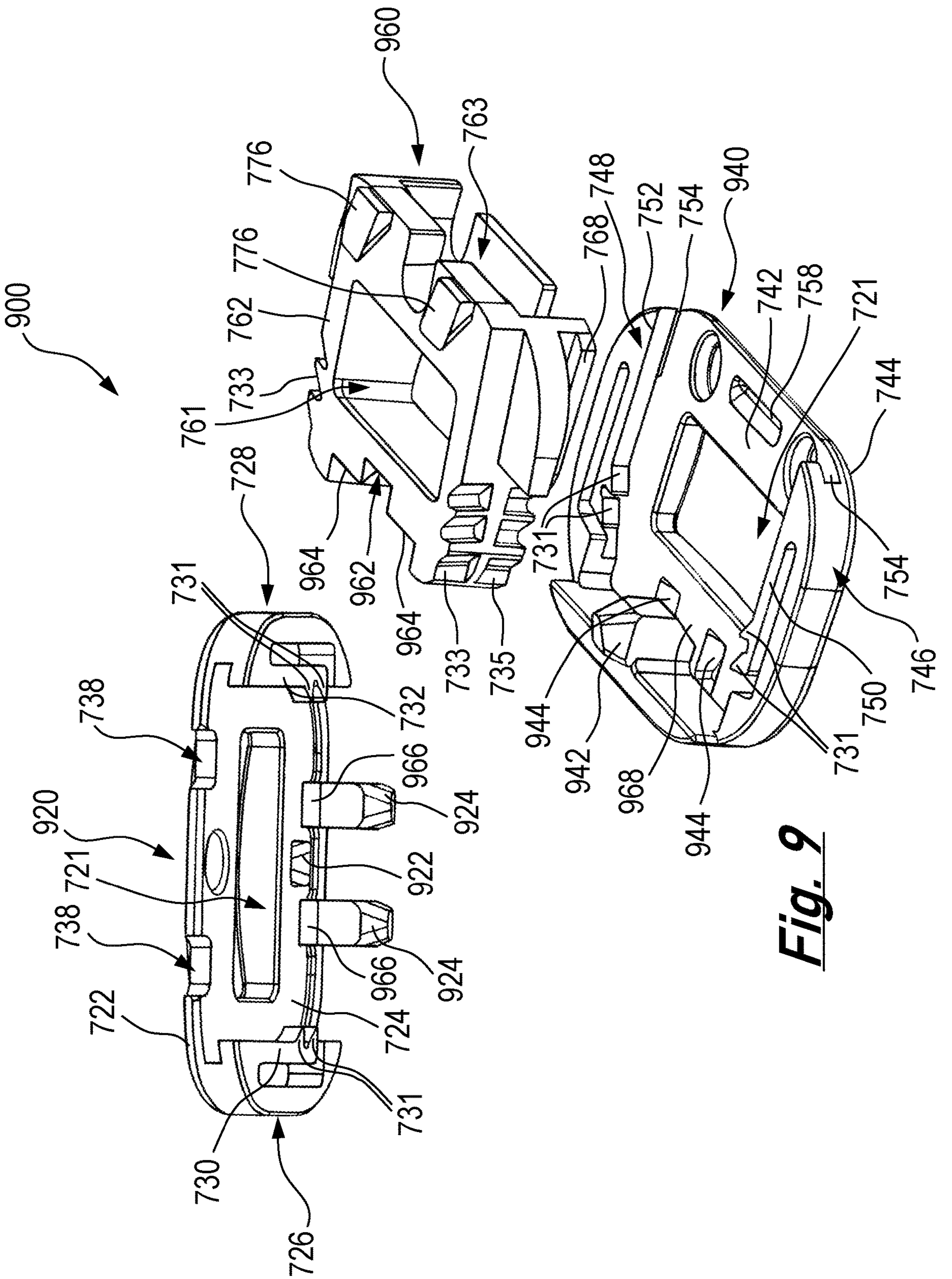
FIG. 9 shows an intervertebral fusion device according to an eighth embodiment.

An eighth embodiment of intervertebral fusion device 900 is shown in FIG. 9. The eighth embodiment 900 has a superior component 920 (which constitutes a superior endplate), an inferior component 940 (which constitutes an inferior endplate), and a core component 960. The eighth embodiment 900 is an anterior lumbar interbody fusion (ALIF) device like the fifth and sixth embodiments. Except as described below, the eighth embodiment is configured in respect of key features in the same fashion as the fifth and sixth embodiments. Such key features are therefore indicated in FIG. 9 by the same reference numerals as for the fifth and sixth embodiments and the reader's attention is directed to the preceding description for a description of such key features.

In respect of differences, as can be seen from FIG. 9, the eighth embodiment 900 lacks the combination of the superior core rear formation 770 and the superior component rear formation 734 and also the combination of the inferior core rear formation 774 and the inferior component rear formation 756. Instead, the inferior component 940 of the eighth embodiment 900 has an upwardly extending post 942 near its posterior edge and an aperture 944 on each side of the upwardly extending post 942. The superior component 920 of the eighth embodiment 900 has an aperture 922 near its posterior edge and a downwardly extending post 924 on each side of the aperture 922. The core component 960 of the eighth embodiment 900 has a core recess 962 which is centrally located in a posterior wall of the core component at the upper side 762. The eighth embodiment 900 is brought into use by positioning the inferior and superior components 920, 940 in the intervertebral space and such that each of the downwardly extending posts 924 is received in a respective one of the two apertures 944 in the inferior component and such that the upwardly extending post 942 is received in the aperture 922 in the superior component 920. Relative movement of the inferior and superior components 920, 940 is thus restricted whilst rotation of an end of each of the downwardly and upwardly extending posts 924, 942 in its respective aperture 922, 944 allows for the inferior and superior components to rotate towards the posterior aspect in relation to each other. The core component 960 is then inserted between the inferior and superior components 920, 940. When the core component 960 is fully received between the inferior and superior components 920, 940, the side of the upwardly extending post 942 is received in the core recess 962. Furthermore, when the core component is fully received, a leading sharp edge 964 on each side of the core recess 962 and at the upper side 762 is received with a recess 966 defined towards the proximal end of a respective one of the two downwardly extending posts 924, to thereby present resistance to separation of the superior component 920 and the core component 960 from each other at the posterior aspect. The upwardly extending post 942 on the inferior component 940 defines a recess 968 towards its proximal end. A sharp edge (not seen in FIG. 9) at the lower side and the posterior aspect of the core component 960 is received in the recess 968 in the upwardly extending post 942 to thereby present resistance to separation of the inferior component 940 and the core component 960 from each other at the posterior aspect.

Each of the first and second superior component profiles 730, 732 of the superior component 920 is in the form of an arm (which constitutes a pawl of a first ratchet). Each arm 730, 732 has two protrusions 731 towards a distal end of the arm. Each of the first and second inferior component profiles 750, 752 of the inferior component 940 is in the form of an arm (which constitutes a pawl of a second ratchet). Each arm 750, 752 has two protrusions 731 towards a distal end of the arm. Turning now to the core component 960, each of two oppositely directed transverse sides of the core component defines an upper set of three recesses 733 and a lower set of three recesses 735 (each set of three recesses constitutes a linear rack of a ratchet). Each set of three recesses 733, 735 extends from a leading end of the core component 960 (i.e. the end of the core component first received between the superior and inferior components or, alternatively, first inserted into the intervertebral space) towards the trailing end of the core component and for about a third of the distance between the leading and trailing ends. When the core component 960 is inserted between the superior and inferior components 920, 940, the two protrusions 731 on each arm 730, 732, 750, 752 are received respectively in two recesses of the respective set of recesses 733, 735 closest to the trailing end of the core component. The core component 960 is thus locked to each of the superior and inferior components 920, 940. When the core component 960 is further inserted between the superior and inferior components 920, 940, the two protrusions 731 on each arm 730, 732, 750, 752 are forced out of their respective recesses with each protrusion then received under spring bias of the arm in the next recess towards the leading end of the core component. The core component 960 is thus locked to each of the superior and inferior components 920, 940 when the core component is fully inserted between the superior and inferior components. Each arm 730, 732, 750, 752 and its respective set of recesses 733, 735 constitutes a ratchet which provides for controlled insertion of the core component between the superior and inferior components.

Figure 10A:
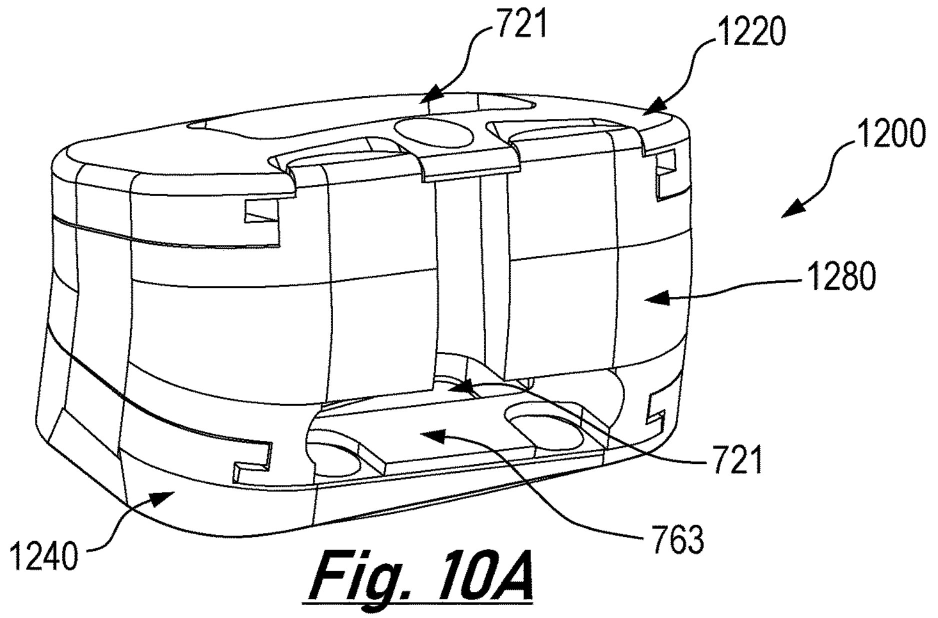
FIG. 10A is a perspective view of a ninth embodiment of the present invention.
Figure 10B:
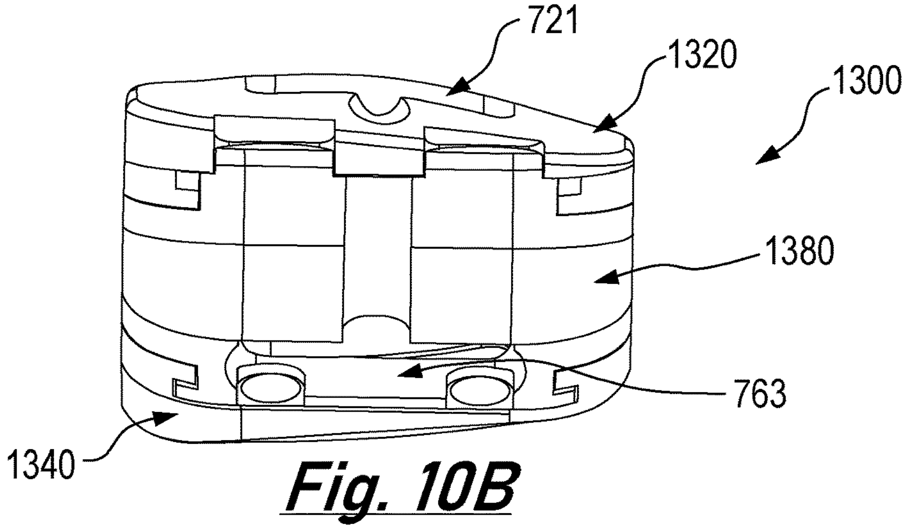
FIG. 10B is a perspective view of a tenth embodiment of the present invention.
Figure 10C:
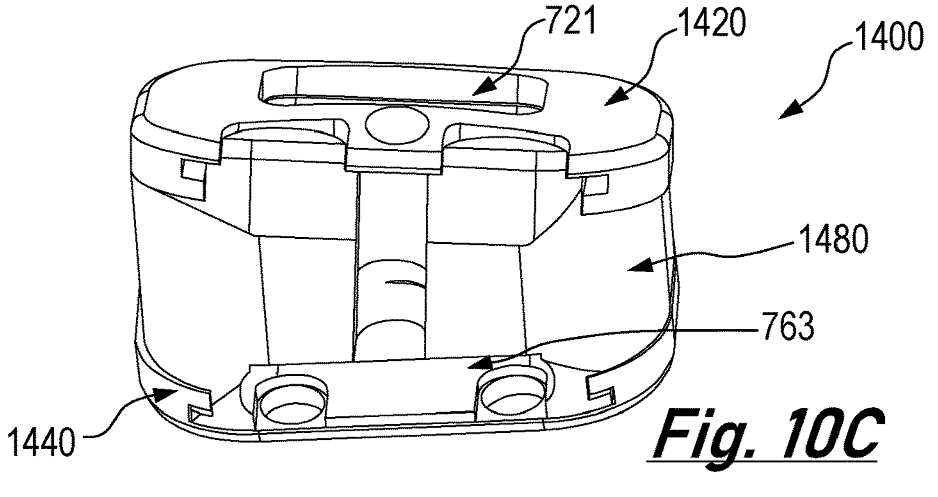
FIG. 10C is a perspective view of an eleventh embodiment of the present invention.

Ninth, tenth and eleventh embodiments of anterior lumbar interbody fusion (ALIF) devices 1200, 1300, 1400 are shown in FIGS. 10A, 10B, and 10C respectively. The sixth embodiment of anterior lumbar interbody fusion (ALIF) device 710 shown in FIGS. 6A and 6B decreases in height from left to right in the coronal direction, i.e. in the direction orthogonal to the direction of insertion of the core component 780 between the superior and inferior components 720, 740, which is in the sagittal direction, and to the direction of separation of the superior and inferior components from each other. The decrease in height of the sixth embodiment of anterior lumbar interbody fusion (ALIF) device 710 is achieved by the superior component 720 decreasing in height from left to right in the coronal direction. With reference to FIG. 5A, the decrease in height of the superior component 720 is achieved by inclination of the superior component top side 722 and the superior component bottom side 724 to each other. In another example, the decrease in height of the anterior lumbar interbody fusion (ALIF) device is from right to left, which is achieved by decrease in height of the core component from right to left.

The ninth embodiment of anterior lumbar interbody fusion (ALIF) device 1200 shown in FIG. 10A comprises a superior component 1220 (which constitutes a superior endplate), an inferior component 1240 (which constitutes an inferior endplate), and a core component 1280. The ninth embodiment of anterior lumbar interbody fusion (ALIF) device 1200 is a further example in which there is decrease in height from left to right in the coronal direction. The decrease in height is achieved by the inferior component 1240 decreasing in height from left to right in the coronal direction. With reference to FIG. 5B, the decrease in height of the inferior component 1240 is achieved by inclination of the inferior component top side 742 and the inferior component bottom side 744 to each other. The effect of the ninth embodiment is the same as the effect of the sixth embodiment.

The tenth embodiment of anterior lumbar interbody fusion (ALIF) device 1300 shown in FIG. 10B comprises a superior component 1320 (which constitutes a superior endplate), an inferior component 1340 (which constitutes an inferior endplate), and a core component 1380. The tenth embodiment of anterior lumbar interbody fusion (ALIF) device 1300 is a further example in which there is decrease in height from left to right in the coronal direction. The decrease in height is achieved by each of the superior component 1320 and the inferior component 1340 decreasing in height from left to right in the coronal direction. With reference to FIG. 5A, the decrease in height of the superior component 1320 is achieved by inclination of the superior component top side 722 and the superior component bottom side 724 to each other. With reference to FIG. 5B, the decrease in height of the inferior component 1340 is achieved by inclination of the inferior component top side 742 and the inferior component bottom side 744 to each other. The effect of the tenth embodiment is the same as the effect of the sixth and ninth embodiments.

The eleventh embodiment of anterior lumbar interbody fusion (ALIF) device 1400 shown in FIG. 10C comprises a superior component 1420 (which constitutes a superior endplate), an inferior component 1440 (which constitutes an inferior endplate), and a core component 1480. The eleventh embodiment of anterior lumbar interbody fusion (ALIF) device 1400 is a further example in which there is decrease in height from left to right in the coronal direction. The decrease in height is achieved by the core component 1480 decreasing in height from left to right in the coronal direction. With reference to FIG. 5C, the decrease in height of the core component 1480 is achieved by inclination of the upper side 762 and the lower side 764 to each other. The effect of the eleventh embodiment is the same as the effect of the sixth, ninth and tenth embodiments. In further embodiments, the core component decreases in height in the coronal direction and at least one of the superior and inferior components decreases in height in the coronal direction. As described above with reference to FIGS. 5 to 6B, the core component 760, 780 has the shape of a frustrum of a wedge whereby the anterior lumbar interbody fusion (ALIF) device decreases in height in the sagittal direction. Embodiments of the anterior lumbar interbody fusion (ALIF) device may thus decrease in height in each of the coronal and sagittal directions.

The invention claimed is:

1. An intervertebral fusion device comprising:

an endplate configured to be received in an intervertebral space defined between first and second vertebrae, the endplate having a leading end and a trailing end;

a core component configured to be received in the intervertebral space, the core component having a leading end and a trailing end; and a ratchet comprising a pawl and a linear rack defining plural recesses, the pawl comprised in one of the core component and the endplate, the linear rack comprised in the other of the core component and the endplate, wherein the core component and the endplate are configured to engage with each other by disposing the leading end of the core component adjacent the trailing end of the endplate and then moving the core component relative to the endplate in a direction of engagement such that the leading end of the core component moves towards the leading end of the endplate and extent of overlap of the core component and the endplate increases, the plural recesses of the linear rack are spaced apart from each other or one another in the direction of engagement such that the plural recesses extend from near or at one of the leading end and the trailing end of the other of the core component and the endplate towards the other of the leading end and the trailing end of the other of the core component and the endplate, the plural recesses extending by no more than 60% of a distance between the leading end and the trailing end of the other of the core component and the endplate, and the ratchet is configured such that the pawl interlocks with each of the plural recesses of the linear rack in turn as the core component is moved further relative to the endplate in the direction of engagement.

2. The intervertebral fusion device according to claim 1, wherein the pawl is integrally formed with the endplate, and the linear rack is integrally formed with the core component.

3. The intervertebral fusion device according to claim 1, wherein the ratchet is a first ratchet, and further comprising a second ratchet, the second ratchet comprising a pawl and a linear rack defining plural recesses spaced apart from each other or one another in the direction of engagement, and the first and second ratchets are spaced apart from each other in a transverse direction.

4. The intervertebral fusion device according to claim 3, wherein the linear racks of the first and second ratchets are spaced apart from each other in the transverse direction and are substantially parallel to each other.

5. The intervertebral fusion device according to claim 1, wherein the pawl comprises a finger which defines at least one protrusion at a distal end of the finger, the finger attached at its proximal end at or near one of the leading end and the trailing end of the one of the core component and the endplate.

6. The intervertebral fusion device according to claim 5, wherein the finger extends in the direction of engagement towards the other of the leading end and the trailing end whereby the distal end of the finger is at or near the other of the leading end and the trailing end.

7. The intervertebral fusion device according to claim 6, wherein the ratchet is a first ratchet, and further comprising a second ratchet, the second ratchet comprising a pawl and a linear rack defining plural recesses spaced apart from each other or one another in the direction of engagement, and the first and second ratchets are spaced apart from each other in a transverse direction, and in which the finger of the first ratchet and a finger of the second ratchet are spaced apart from each other in the transverse direction and are substantially parallel to each other.

8. The intervertebral fusion device according to claim 7, wherein the at least one protrusion of the finger of the first ratchet and at least one protrusion of the finger of the second ratchet protrude towards each other, and the core component and the endplate are configured such that the fingers of the first and second ratchets flex resiliently apart from each other in the transverse direction as the core component moves relative to the endplate in the direction of engagement and before the pawl interlocks with the plural recesses of the linear rack.

9. The intervertebral fusion device according to claim 7, wherein the core component and the endplate are configured such that lateral sides of the core component are received between and are adjacent the fingers of the first and second ratchets to thereby guide movement of the core component relative to the endplate, the lateral sides extending in the direction of engagement.

10. The intervertebral fusion device according to claim 5, wherein the finger defines plural protrusions towards a distal end of the finger, the plural protrusions spaced apart from each other or one another in the direction of engagement, the finger defining a first number of protrusions and the linear rack defining a second number of recesses, the second number being greater than the first number.

11. The intervertebral fusion device according to claim 1, wherein the core component and the endplate are configured to inter-engage whereby there is movement of the core component and the endplate in the direction of engagement, and movement in a direction of separation of the first and second vertebrae is prevented.

12. The intervertebral fusion device according to claim 11, wherein the core component defines an elongate protrusion on each lateral side, the endplate defines a keyway towards each lateral side, and each elongate protrusion is slidably received in a respective one of the keyways, the lateral sides extending in the direction of engagement whereby the elongate protrusions and the keyways extend in the direction of engagement.

13. The intervertebral fusion device according to claim 1, wherein the endplate is an inferior endplate, the linear rack is comprised in the core component and the pawl is comprised in the inferior endplate.

14. The intervertebral fusion device according to claim 1 comprising a second endplate comprised in and integrally formed with the core component.

15. The intervertebral fusion device according to claim 1 comprising a second endplate, the core component configured to be received between and to engage with the first and second endplates by movement of the core component relative to the first and second endplates.

16. The intervertebral fusion device according to claim 15, wherein lateral sides of the core component extend in the direction of engagement and are snugly received between opposing walls defined by the second endplate whereby the core component is guided to move slidably relative to the second endplate in the direction of engagement.

17. The intervertebral fusion device according to claim 15, wherein the pawl and the linear track are comprised in the core component and one of the first and second endplates.

18. The intervertebral fusion device according to claim 17, wherein the core component and the other of the first and second endplates comprise a further pawl and a single recess, the further pawl interlocking with the single recess when the core component and the other of the first and second endplates are substantially in registration with each other.

19. The intervertebral fusion device according to claim 1, wherein the core component and the endplate are configured to lock together when they are in registration with each other to prevent movement in a direction of separation of the first and second vertebrae.

20. The intervertebral fusion device according to claim 1, wherein each of the plural recesses is defined by first and second generally opposing surfaces, one of the first and second surfaces facing in the direction of engagement and the other of the first and second surfaces facing against the direction of engagement, and a part of the pawl is received between the first and second surfaces when the pawl interlocks with a recess of the plural recesses.

21. The intervertebral fusion device according to claim 1, wherein the pawl comprises a finger attached at its proximal end to the one of the core component and the endplate, the finger flexing resiliently during movement of the core component relative to the endplate in the direction of engagement and before the pawl interlocks with the plural recesses of the linear rack whereby a part of the finger towards its distal end is urged into each of the plural recesses in turn.

22. The intervertebral fusion device according to claim 21, wherein the other of the core component and the endplate defines a flexing surface against which the finger towards its distal end abuts and moves along during movement of the core component relative to the endplate in the direction of engagement whereby the distal end of the finger is displaced in a transverse direction to thereby resiliently flex the finger and before the part of the finger towards its distal end interlocks with the plural recesses of the linear rack.

23. A method of installing an intervertebral fusion device in an intervertebral space defined between first and second vertebrae, the intervertebral fusion device comprising an endplate having a leading end and a trailing end, a core component having a leading end and a trailing end, and a ratchet comprising a pawl and a linear rack defining plural recesses, the pawl comprised in one of the core component and the endplate, the linear rack comprised in the other of the core component and the endplate, the plural recesses spaced apart from each other or one another in a direction of engagement of the core component with the endplate such that the plural recesses extend from near or at one of the leading end and the trailing end of the other of the core component and the endplate towards the other of the leading end and the trailing end of the other of the core component and the endplate, the plural recesses extending by no more than 60% of a distance between the leading end and the trailing end of the other of the core component and the endplate, the method comprising:

disposing the leading end of the core component adjacent the trailing end of the endplate;

bringing the core component into engagement with the endplate by moving the core component relative to the endplate in the direction of engagement such that the leading end of the core component moves towards the leading end of the endplate and extent of overlap of the core component and the endplate increases; and further moving the core component relative to the endplate in the direction of engagement whereby the pawl interlocks with each of the plural recesses of the linear rack in turn until the core component and the endplate have a desired extent of overlap; and installing the endplate and the core component in the intervertebral space.

24. An intervertebral fusion device, comprising:

an endplate configured to be received in an intervertebral space defined between first and second vertebrae, the endplate having a leading end and a trailing end;

a core component configured to be received in the intervertebral space, the core component having a leading end and a trailing end; and at least one ratchet, each at least one ratchet comprising a pawl and a linear rack defining plural recesses, the pawl comprised in one of the core component and the endplate, the linear rack comprised in the other of the core component and the endplate, wherein the pawl comprises a finger which defines at least one protrusion at a distal end of the finger, the finger attached at its proximal end at or near one of the leading end and the trailing end of the one of the core component and the endplate, wherein the finger defines plural protrusions towards a distal end of the finger, the finger defining a first number of protrusions and the linear rack defining a second number of recesses, the second number being greater than the first number, wherein the core component and the endplate are configured to engage with each other by disposing the leading end of the core component adjacent the trailing end of the endplate and then moving the core component relative to the endplate in a direction of insertion such that the leading end of the core component moves towards the leading end of the endplate and extent of overlap of the core component and the endplate increases, the plural recesses of the linear rack extend in the direction of insertion and from near or at one of the leading end and the trailing end of the other of the core component and the endplate towards the other of the leading end and the trailing end of the other of the core component and the endplate, the plural recesses extending by no more than 60% of a distance between the leading end and the trailing end of the other of the core component and the endplate, and the at least one ratchet is configured such that the pawl starts to inter-engage with the plural recesses of the linear rack as the core component is moved further relative to the endplate in the direction of insertion.

* * * * *